US011445997B2

(12) United States Patent
Avula et al.

(10) Patent No.: US 11,445,997 B2
(45) Date of Patent: Sep. 20, 2022

(54) ULTRASOUND IMAGING OF BIOMARKER SENSITIVE HYDROGELS

(71) Applicants: UNIVERSITY OF UTAH RESEARCH FOUNDATION, Salt Lake City, UT (US); Sentiomed, Inc., Salt Lake City, UT (US)

(72) Inventors: Mahender nath Avula, South Jordan, UT (US); Douglas A. Christensen, Salt Lake City, UT (US); Navid Farhoudi, Salt Lake City, UT (US); Stan Kanarowski, Park City, UT (US); Julia Koerner, Salt Lake City, UT (US); Jules John Magda, Salt Lake City, UT (US); Rami Sami Marrouche, Salt Lake City, UT (US); Christopher F. Reiche, Salt Lake City, UT (US); Florian Solzbacher, Salt Lake City, UT (US); Michael David Sorenson, Salt Lake City, UT (US)

(73) Assignees: UNIVERSITY OF UTAH RESEARCH FOUNDATION, Salt Lake City, UT (US); SENTIOMED, INC., Salt Lake City, UT (US)

( * ) Notice: Subject to any disclaimer, the term of this patent is extended or adjusted under 35 U.S.C. 154(b) by 413 days.

(21) Appl. No.: 16/330,048

(22) PCT Filed: Sep. 1, 2017

(86) PCT No.: PCT/US2017/049944
§ 371 (c)(1),
(2) Date: Mar. 1, 2019

(87) PCT Pub. No.: WO2018/045333
PCT Pub. Date: Mar. 8, 2018

(65) Prior Publication Data
US 2019/0192113 A1 Jun. 27, 2019

Related U.S. Application Data

(60) Provisional application No. 62/383,344, filed on Sep. 2, 2016, provisional application No. 62/435,491, filed
(Continued)

(51) Int. Cl.
*A61B 5/00* (2006.01)
*A61B 8/08* (2006.01)
(Continued)

(52) U.S. Cl.
CPC .............. *A61B 8/0841* (2013.01); *A61B 8/12* (2013.01); *A61B 8/481* (2013.01); *A61B 90/39* (2016.02); *A61B 2090/3929* (2016.02)

(58) Field of Classification Search
CPC ..... A61B 8/0841; A61B 8/5223; A61B 90/39; A61B 8/481; A61B 2090/3929; A61K 49/226
See application file for complete search history.

(56) References Cited

U.S. PATENT DOCUMENTS

2002/0042065 A1* 4/2002 Han ................. G01N 33/54373
435/6.11
2003/0100822 A1* 5/2003 Lew .................. A61B 5/14539
600/365
(Continued)

OTHER PUBLICATIONS

Ritcher et al., "Reviewon Hydrogel-based pH Sensors and Microsensors", Sensors 2008, vol. 8 No. 1, p. 561-581 (Year: 2008).*
(Continued)

*Primary Examiner* — Joel F Brutus
(74) *Attorney, Agent, or Firm* — Workman Nydegger

(57) ABSTRACT

Systems and methods for accurately measuring changes in biomarker sensitive hydrogel volume and shape due to
(Continued)

exposure to various biomarkers include a system for identifying one or more dimensional changes in a biomarker sensitive hydrogel positioned within an in vivo environment. The system includes a biomarker sensitive hydrogel positioned within an in vivo environment and configured to dimensionally change in response to interaction with predefined biomarkers. The system additionally includes an ultrasound transducer for locating and identifying one or more characteristics of the biomarker sensitive hydrogel and a computer system in electrical communication with the ultrasound transducer. The computer system is configured to receive characteristics of the biomarker sensitive hydrogel from the ultrasound transducer and determine dimensional changes of the biomarker sensitive hydrogel based on the received characteristics.

22 Claims, 13 Drawing Sheets

Related U.S. Application Data on Dec. 16, 2016, provisional application No. 62/435,537, filed on Dec. 16, 2016, provisional application No. 62/518,456, filed on Jun. 12, 2017, provisional application No. 62/518,491, filed on Jun. 12, 2017, provisional application No. 62/552,623, filed on Aug. 31, 2017.

(51) Int. Cl.
  *A61B 8/12* (2006.01)
  *A61B 90/00* (2016.01)

(56) References Cited

U.S. PATENT DOCUMENTS

| | | | |
|---|---|---|---|
| 2007/0239016 A1 | 10/2007 | Fisher | |
| 2009/0170124 A1* | 7/2009 | Campbell | G01N 33/56911 435/7.2 |
| 2013/0245402 A1 | 9/2013 | Ziaie et al. | |
| 2013/0338503 A1 | 12/2013 | Cohen | |
| 2014/0182361 A1* | 7/2014 | Bargatin | G01N 29/34 73/61.79 |
| 2015/0087978 A1* | 3/2015 | Wada | A61B 8/44 600/440 |
| 2016/0015323 A1 | 1/2016 | Tathireddy et al. | |
| 2016/0033389 A1 | 2/2016 | Serpe | |
| 2020/0093408 A1 | 3/2020 | Solzbacher et al. | |
| 2021/0267573 A1 | 9/2021 | Reiche et al. | |
| 2021/0338195 A1 | 11/2021 | Reiche et al. | |

OTHER PUBLICATIONS

Millet et al., "Characterization of Mass and Swelling of Hydrogel Microstructures using MEMS Resonant Mass Sensor Arrays", Nano, Micro, Small vol. 8 iss. 16, (Aug. 20, 2012), p. 2555-2562 (Year: 2012).*

Sannino et al., "Spin coating cellulose derivatives on quartz crystal microbalance plates to obtain hydrogel-based fast sensors and actuators", Journal of Applied Polymer Science vol. 106 iss. 5, (Dec. 5, 2007), p. 3040-3050 (Year: 2007).*

Rey et al., "Monitoring swelling and deswelling of thin polymer films by microcantilever sensors", Sensors and Actuators B: Chemical, (2014), p. 602-610 (Year: 2014).*

Park J H et al.: "A wireless chemical sensing scheme using ultrasonic imaging of microbubble embedded hydrogel", 2015 Transducer—2015 18th International Conference on Solid-State Sensors, Actuators and Microsystems (Transducers), IEEE, Jun. 21, 2015 (Jun. 21, 2015), pp. 2220-2223, XP033189786, DOI: 10.1109/Transducers.2015.7181402 [retrieved on Aug. 5, 2015].

International Search Report and Written Opinion, PCT/US2017/049944, United States International Search Authority, Completed Oct. 20, 2017.

International Search Report and Written Opinion issued in PCT/US2018/037166 dated Sep. 11, 2018.

Tavakoli et al. "Hydrogel Based Sensors for Biomedical Applications: An Updated Review" Polymers 2017, 9, 364.

* cited by examiner

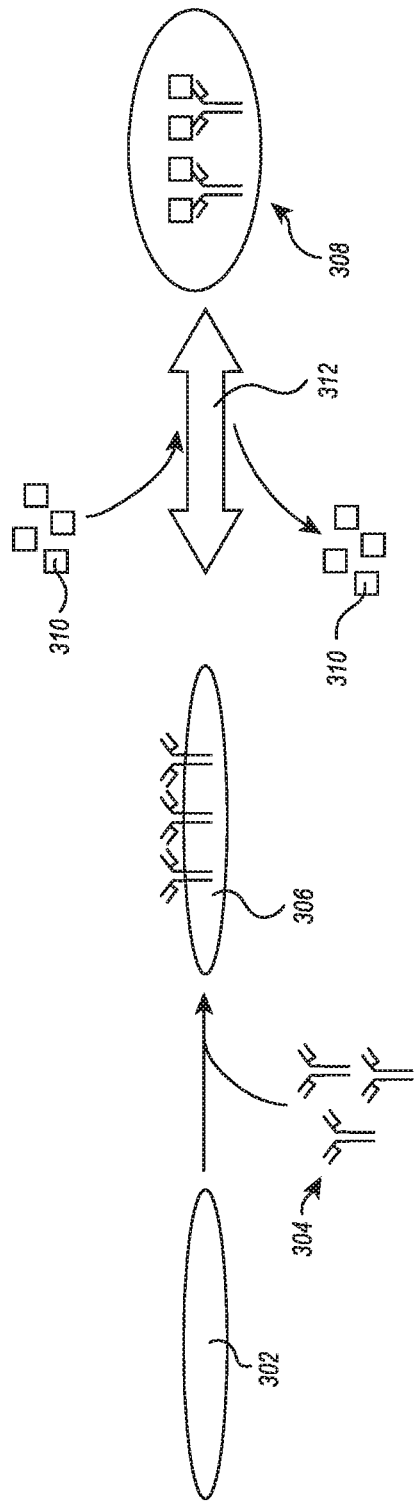
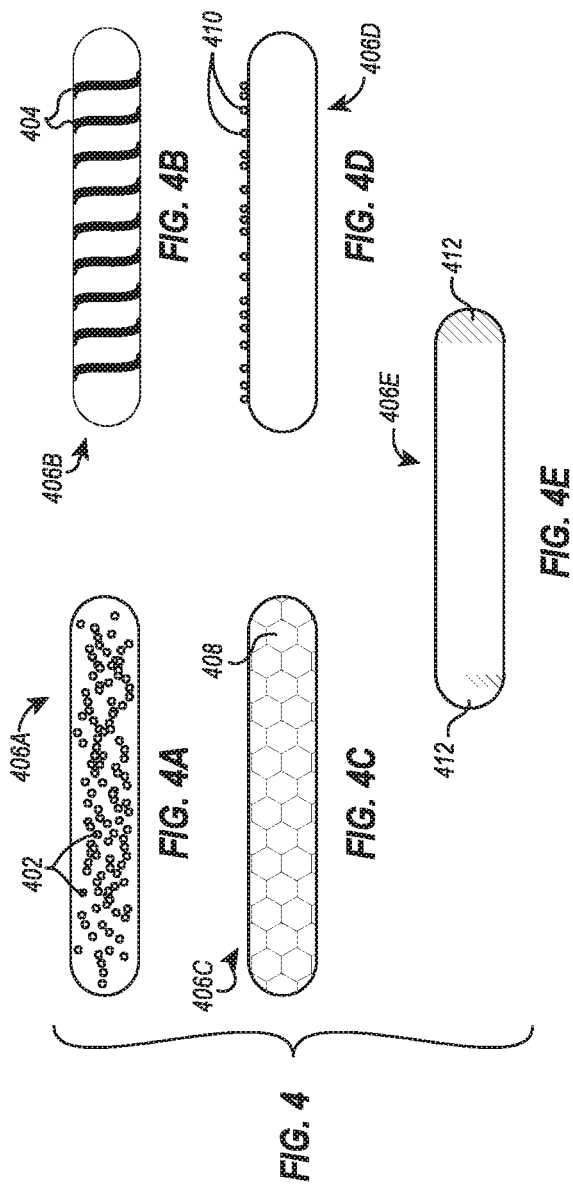
FIG. 3
FIG. 4A
FIG. 4B
FIG. 4C
FIG. 4D
FIG. 4E
FIG. 4

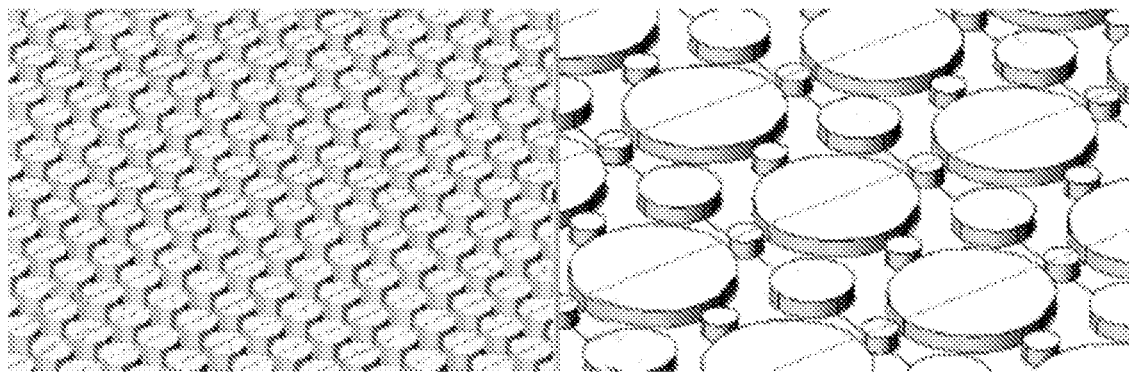
FIG. 17A    FIG. 17B
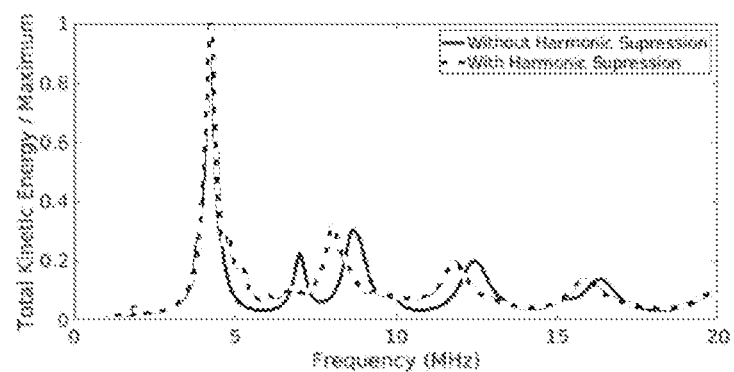
FIG. 18
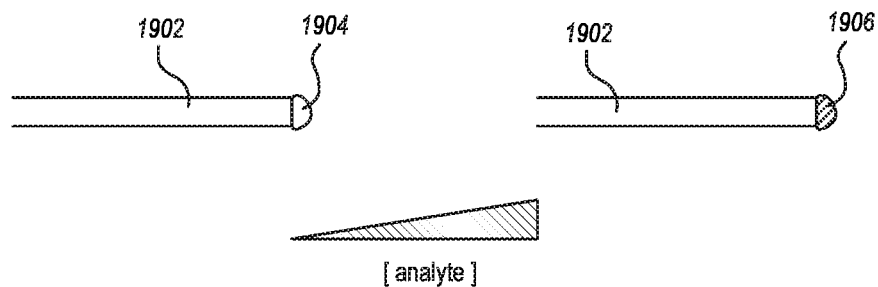
FIG. 19

ULTRASOUND IMAGING OF BIOMARKER SENSITIVE HYDROGELS

This application claims priority to PCT Application No. PCT/US2017/049944 filed Sep. 1, 2017, entitled "ULTRASOUND IMAGING OF BIOMARKER SENSITIVE HYDROGELS," which claims the benefit of and priority to U.S. Provisional Patent Application Ser. No. 62/383,344, filed Sep. 2, 2016 and titled "ULTRASOUND BASED TRANSDUCER MECHANISM FOR HYDROGEL SENSORS," U.S. Provisional Patent Application No. 62/435,491, filed Dec. 16, 2016 and titled "HYDROGEL ULTRASOUND RESONATORS FOR BIOMARKER SENSING," U.S. Provisional Patent Application No. 62/435,537, filed Dec. 16, 2016 and titled "NOVEL METHODS TO DETECT VOLUME CHANGES OF HYDROGELS USING ULTRASOUND," U.S. Provisional Patent Application No. 62/518,456, filed Jun. 12, 2017 and titled "METHODS TO DETECT VOLUME CHANGES OF HYDROGELS USING ULTRASOUND," U.S. Provisional Patent Application No. 62/518,491, filed Jun. 12, 2017 and titled "METHODS TO DETECT VOLUME CHANGES OF HYDROGELS USING ULTRASOUND," and U.S. Provisional Patent Application No. 62/552,623, filed Aug. 31, 2017 and titled "HYDROGEL ULTRASOUND RESONATORS FOR BIOMARKER SENSING." All of the aforementioned are incorporated herein by reference in their entirety.

GOVERNMENT LICENSE RIGHTS

This invention was made with government support under grant number EB008571 awarded by the National Institutes of Health. The government has certain rights in the invention.

BACKGROUND

Technical Field

This disclosure generally relates to medical imaging. More specifically, the present disclosure relates to using ultrasound to view and measure biomarker sensitive hydrogels in vivo.

Related Technology

Advances in computing technology have resulted in a concomitant advance in medical device technologies, including within the field of diagnostic and interventional medicine. Particularly, the past century has demonstrated significant advances in medical imaging devices. Such advances have been hallmarked by the advent of radiologic devices such as computed tomography, magnetic resonance imaging, ultrasound, and other imaging devices that allow for the non-invasive viewing and exploration of internal structures of the body. These devices are often utilized within interventional radiology and minimally invasive surgeries as well, providing image guidance for any of a plethora of medical devices operated by the physician.

The non-invasive nature of medical imaging devices provide certain advantages, but they also have their limitations. Magnetic resonance imaging, for example, requires a patient to hold completely still in a confined area while the overly large, loud, and expensive imaging machine obtains imaging data. Other medical imaging devices, such as those utilized for medical ultrasound, are less expensive but often cannot provide high-resolution images of deep tissue sites.

Further, medical imaging devices are limited by the kind of information reported. Ultrasound, for example, generally relies on sonically reflective surfaces to produce an image and provides little information outside of the image data that can be derived from sonically reflective surfaces within the body. In some instances, ultrasound can be used to detect and monitor blood flow and heart rate, but ultrasound lacks the resolving power to identify the presence or absence—let alone the concentration—of biomarkers within the body. The other medical imaging techniques and devices available similarly lack the ability to identify biomarkers within the body, and while the medical imaging devices developed over the past century have allowed physicians and clinicians to better document, treat, and understand pathologies, they have their limits.

Accordingly, there are a number of disadvantages with medical imaging devices that can be addressed.

BRIEF SUMMARY

Implementations of the present disclosure solve one or more of the foregoing or other problems in the art with medical imaging devices. In particular, one or more implementations can include a system for identifying one or more dimensional changes in a biomarker sensitive hydrogel positioned within an in vivo environment using ultrasound. The system includes a biomarker sensitive hydrogel positioned within an in vivo environment and configured to dimensionally change in response to interaction with one or more predefined biomarkers. The system additionally includes an ultrasound transducer for locating and identifying one or more characteristics of the biomarker sensitive hydrogel and a computer system in electrical communication with the ultrasound transducer. The computer system includes one or more processors and is configured to receive the one or more characteristics of the biomarker sensitive hydrogel from the ultrasound transducer and to determine, at the one or more processors, one or more dimensional changes of the biomarker sensitive hydrogel based on the received one or more characteristics of the biomarker sensitive hydrogel.

In some implementations, the computer system receives the one or more characteristics of the biomarker sensitive hydrogel from the ultrasound transducer at a first time and at a second time. Based on differences between the one or more characteristics of the biomarker sensitive hydrogel at the first time and at the second time, the computer system determines, at the one or more processors, the one or more dimensional changes of the biomarker sensitive hydrogel. The biomarker sensitive hydrogel can include one or more markers or contrast agents, and the differences between the one or more characteristics of the biomarker sensitive hydrogel at the first time and at the second time can be (i) a change in an average density of one or more markers or contrast agents or (ii) a distance between at least two markers or contrast agents of the one or more markers or contrast agents.

In some implementations, a system for identifying one or more changes in a biomarker sensitive hydrogel positioned within an in vivo environment further comprises a control hydrogel positioned within the in vivo environment, the control hydrogel configured not to dimensionally change in response to interaction with one or more predefined biomarkers. The ultrasound transducer is further configured to locate the control hydrogel and identify one or more control characteristics of the control hydrogel. Accordingly, the computer system is further configured to receive the one or more control characteristics from the ultrasound transducer and determine, at the one or more processors, one or more dimensional changes of the biomarker sensitive hydrogel based on differences between the one or more characteristics of the biomarker sensitive hydrogel and the one or more control characteristics of the control hydrogel. The biomarker sensitive hydrogel and the control hydrogel can each comprise one or more markers or contrast agents. The one or more markers or contrast agents can comprise one or more of: a metal, a plurality of microspheres, a plurality of microbubbles, a plurality of microwires, a plurality of nanowires, or a plurality of sonically reflective nanoparticles. The one or more markers or contrast agents can additionally be positioned to render a plurality of barber pole stripes along or within the biomarker sensitive hydrogel and the control hydrogel or be positioned to render one or more foci along or within the biomarker sensitive hydrogel and the control hydrogel.

In some implementations, the biomarker sensitive hydrogel comprises an elongate shape between 10-100 μm thick and 2-20 mm long, and the one or more dimensional changes of the biomarker sensitive hydrogel comprise a change in the volume of the biomarker sensitive hydrogel. The change in volume causes a detectable change in the length of the biomarker sensitive hydrogel, which correlates with the concentration of predefined biomarkers interacting with the biomarker sensitive hydrogel.

In some implementations, the one or more characteristics of the biomarker sensitive hydrogel comprise first and second sets of characteristics of the biomarker sensitive hydrogel. The first set of characteristics of the biomarker sensitive hydrogel correspond to a first view of the biomarker sensitive hydrogel within the in vivo environment, and the second set of characteristics of the biomarker sensitive hydrogel correspond to a second view of the biomarker sensitive hydrogel within the in vivo environment where the second view is substantially orthogonal to the first view.

One or more implementations can include a system for detecting a concentration of one or more biomarkers within an in vivo environment. The system can include (i) an ultrasound transducer, (ii) a sleeve that selectively surrounds at least a distal end of the ultrasound transducer, and (iii) a computer system in electrical communication with the ultrasound transducer. The sleeve comprises a hydrogel resonator sheet configured to absorb a subset of ultrasonic frequency bands emitted by the ultrasound transducer. The hydrogel resonator sheet comprises a biomarker sensitive hydrogel arranged in an array of acoustic resonators that undergo one or more physical changes in response to a selective association with the one or more biomarkers. The computer system includes one or more processors and is configured to receive one or more characteristics of at least a portion of the array of acoustic resonators from the ultrasound transducer and to determine, at the one or more processors, one or more changes of the hydrogel resonator sheet based on the received one or more characteristics of the portion of the array of acoustic resonators.

In some implementations, the computer system is additionally configured to receive a plurality of ultrasound frequencies from the ultrasound transducer that are outside the subset of ultrasonic frequency bands, and by processing at least a portion of the plurality of ultrasound frequencies outside the subset of ultrasonic frequency bands, the computer system is configured to construct an image the in vivo environment using the one or more processors.

In some implementations, the one or more characteristics received from the ultrasound transducer comprise a shift in a frequency position of the maxima of the absorption (or any other significant point of the frequency spectrum) for the portion of the array of resonators, and as determined by the shift in the frequency position of the maxima of the absorption for the portion of the array of resonators, the one or more changes of the hydrogel resonator sheet comprise a swelling or a shrinking of at least the portion of the array of resonators.

In some implementations, the hydrogel resonator sheet is spatially associated with a contrast structure, and the computer system is additionally configured to receive spatial information associated with the contrast structure from the ultrasound transducer. Additionally, the computer system can determine the dimensional changes of the biomarker sensitive hydrogel based on the spatial information associated with the contrast structure and the received one or more characteristics between a first point in time and a second point in time.

In some implementations, the array of acoustic resonators comprises a periodic array of same-sized acoustic resonators.

In some implementations, the array of acoustic resonators comprises a repeated pattern of cylindrical ultrasonic resonators to enable selective harmonic suppression. The repeated pattern can include, in a first direction, a central cylindrical ultrasonic resonator having a first size alternating with a second cylindrical ultrasonic resonator having a second size. The repeated pattern can additionally include, in a second direction, the central cylindrical ultrasonic resonator alternating with a third cylindrical ultrasonic resonator having a third size.

In some embodiments, the sleeve further includes a control array of resonators that do not undergo one or more physical changes in response to interaction with predefined biomarkers. The ultrasound transducer is configured to identify control characteristics of the control array of resonators, and the computer system is further configured to receive, from the ultrasound transducer, the control characteristics and determine changes, at the one or more processors, based on differences between the characteristics of the portion of the array of acoustic resonators and the control characteristics of the control array of resonators.

One or more implementations can include a biosensor that provides an ultrasound-dependent readout of biomarker concentration within an in vivo environment. The biosensor can include a chip having a contrast structure disposed on a bottom portion and a hydrogel resonator sheet configured to absorb a subset of ultrasonic frequency bands emitted by an ultrasound transducer. The hydrogel resonator sheet can be associated with a top portion of the chip and positioned above the contrast structure. The contrast structure additionally includes a plurality of spatially rigid reference points for comparing dimensional changes of the hydrogel resonator sheet.

One or more implementations can include a computer-implemented method for using ultrasound to identify one or more changes in a biomarker sensitive hydrogel positioned within an in vivo environment. The computer-implemented method can include receiving data from an ultrasound receiver at a first time, the data comprising one or more characteristics of the biomarker sensitive hydrogel, and determining one or more of a volume or length of the biomarker sensitive hydrogel based on the one or more characteristics. The computer-implemented method can additionally include receiving additional data from the ultrasound receiver at a second time, the additional data comprising one or more updated characteristics of the biomarker sensitive hydrogel, and determining one or more of an updated volume or an updated length of the biomarker sensitive hydrogel based on the one or more updated characteristics. Based on the volume, the length, the updated volume, and the updated length, the computer-implemented method can additionally include calculating the dimensional changes of the biomarker sensitive hydrogel.

Accordingly, systems for identifying one or more changes in a biomarker sensitive hydrogel positioned within an in vivo environment, systems for detecting a concentration of one or more biomarkers within an in vivo environment, and computer-implemented methods for using ultrasound to identify one or more changes in a biomarker sensitive hydrogel positioned within an in vivo environment are disclosed.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope.

In the drawings, multiple instances of an element may each include separate letters appended to the element number. For example, two instances of a particular element "100" may be labeled as "100a" and "100b." In that case, the element label may be used without an appended letter (e.g., "100") to generally refer to every instance of the element, while the element label will include an appended letter (e.g., "100a") to refer to a specific instance of the element. Similarly, a drawing number may include separate letters appended thereto. For example, FIG. 2 may include FIG. 2A and FIG. 2B. In that case, the drawing number may be used without the appended letter (e.g., FIG. 2) to generally refer to every instance of the drawing, while the drawing label will include an appended letter (e.g., FIG. 2A) to refer to a specific instance of the drawing. The disclosure will be described and explained with additional specificity and detail through the use of the accompanying drawings in which:

FIG. 3 illustrates a simplified model of the generation and reversible swelling of biomarker sensitive hydrogels that utilize antibody mediated biomarker recognition.

FIG. 4A illustrates an exemplary biomarker sensitive hydrogel having a plurality of microbubbles dispersed throughout the biomarker sensitive hydrogel.

FIG. 4B illustrates an exemplary biomarker sensitive hydrogel having a plurality of barber pole stripes disposed along the biomarker sensitive hydrogel.

FIG. 4C illustrates an exemplary biomarker sensitive hydrogel having a sonically reflective and flexible sleeve associated therewith.

FIG. 4D illustrates an exemplary biomarker sensitive hydrogel having a plurality of nanoparticles overlain on a surface of the biomarker sensitive hydrogel.

FIG. 4E illustrates an exemplary biomarker sensitive hydrogel having a pair of contrast-laden foci disposed on opposite ends of the biomarker sensitive hydrogel.

FIG. 17A illustrates an exemplary hydrogel resonator array.

FIG. 17B illustrates an exemplary hydrogel resonator array with harmonic suppressors.

FIG. 18 is a graph illustrating the total kinetic energy of the arrays illustrated in FIGS. 17A and 17B along a frequency spectrum.

FIG. 19 illustrates a fiber optic cable associated with a biomarker sensitive hydrogel that changes optical properties in response to changes in perceived analyte concentration.

DETAILED DESCRIPTION

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the terminology used herein is for the purpose of describing the embodiments, and is not necessarily intended to limit the scope of the claimed invention.

Ultrasound and Hydrogel Sensing

As discussed above, medical imaging devices are generally limited in the kind information that can be reported. Ultrasound, for example, generally relies on sonically reflective surfaces to produce an image and provides little information outside of image data. Particularly, ultrasound lacks the resolving power to identify the presence or absence—let alone the concentration—of biomarkers within the body. Other advancements, however, can be adapted for this purpose. One such example includes hydrogels.

Hydrogels are objects consisting of hydrophilic cross-linked networks of polymer that have both liquidlike and solidlike properties. Smart hydrogels characteristically experience a change in their volume and mechanical properties in response to the presence of a specific stimulus or analyte. As used herein, the term "analyte" includes any substance that can itself be identified or measured or of which a chemical or physical property thereof can be identified or measured. Analytes include, for example, nucleic acids, proteins, chemicals, or other compounds. In some instances, analytes serve as a physiologic, pathologic, or environmental marker of a known or unknown phenomenon (e.g., insulin levels can serve as a biomarker for diabetes). Hydrogels that are responsive to one or more biomarkers are termed "biomarker sensitive hydrogels," and although much of the disclosure herein particularly recites "a biomarker sensitive hydrogel," it should be appreciated that the disclosed embodiments apply generally to smart hydrogels that are responsive to any analyte.

Hydrogels can also respond to the presence of an environmental stimulus (e.g., temperature, pH, gas, osmolarity, humidity, etc.) and can additionally serve to indicate particular state data of an aqueous solution, such as pH. That is, hydrogels can change their volume and mechanical properties in response to the level of salinity or acidity in an aqueous solution.

Figure 1:
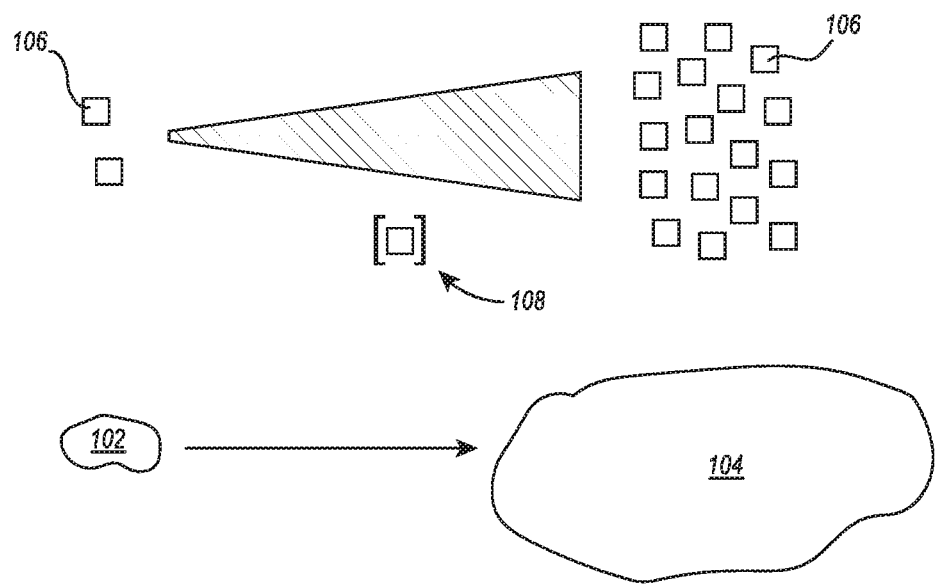
FIG. 1 illustrates a diagram representing the analyte-concentration-dependent or stimulus-intensity-dependent swelling of hydrogels.

FIG. 1 illustrates the characteristic change in volume exhibited by hydrogels. As shown, a hydrogel can transition from a collapsed or shrunken state 102 to a swollen state 104 in response to the presence of a specific analyte 106. Although seemingly depicted as a binary transition—from a shrunken state 102 to a swollen state 104—the change in volume exhibited by hydrogels is typically not binary, just as a change in analyte availability is also often not represented as a binary modality. As shown, the concentration 108 of the analyte 106 can span any point along a spectrum from low to high concentration. Advantageously, hydrogels respond to variable analyte concentrations in a similar graded fashion. Instead of being a binary readout of the presence or absence of an analyte or stimulus, hydrogels experience a change in volume that correlates with the concentration of analyte interacting with the hydrogel.

Figure 2:
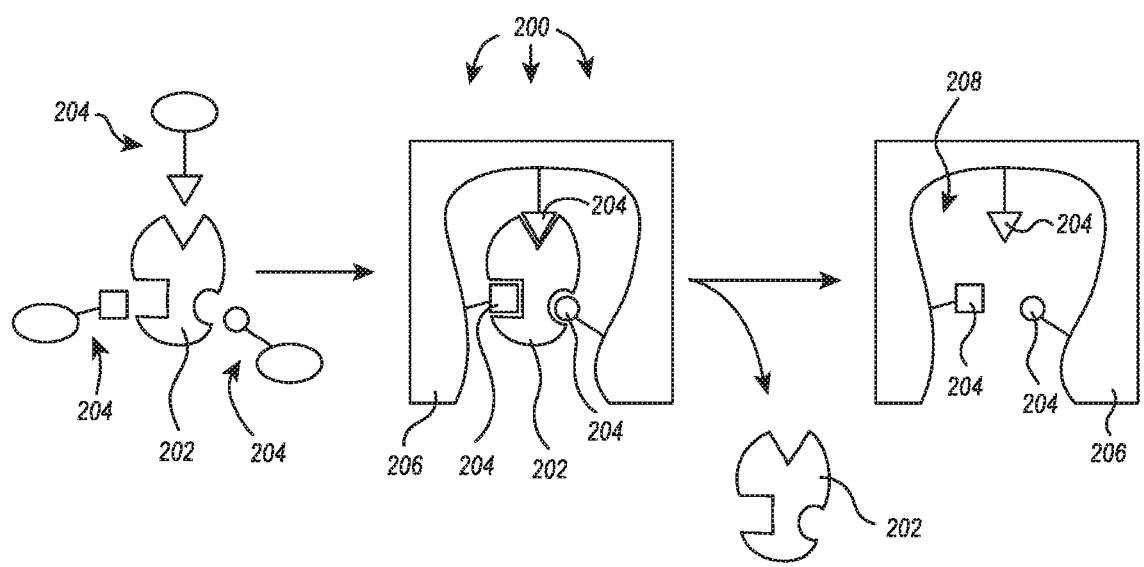
FIG. 2 illustrates a simplified model of molecular imprinting as relevant to generation of one or more types of biomarker sensitive hydrogels.

Hydrogels can sense analytes and/or stimuli using a variety of recognition domains, and the binding specificity and fidelity can be tuned to various sensitives, often depending on the type of recognition domain utilized. FIG. 2 illustrates a generalized method 200 of molecular imprinting that can be used to manufacture hydrogels with specificity for a given analyte. Molecular imprinting relies on a combination of reversible binding and shape complementarity to specifically recognize target analytes. Referring to FIG. 2, the first step of the illustrated method 200 is allow functional monomers 204 to interact with and self-assemble about a print molecule 202. The print molecule 202 includes the same desired shape as the target analyte such that when the functional monomers 204 self-assemble and are polymerized, the resulting molecular imprinted polymer 206 includes a cavity 208 that is complementary in size and shape to the print molecule. The print molecules can be removed from the molecular imprinted polymer 206, leaving the cavity 208 to function as a selective binding site for the specific analyte.

Hydrogels can be made to include a variety of additional or alternative analyte recognition domains, such as antibodies nucleic acid based aptamers. Antibodies traditionally demonstrate a high level of specificity for targets and are good receptors for biomarkers. Advantageously, antibody binding of biomarkers is a reversible process, and when incorporated into a hydrogel, the resultant biomarker sensitive hydrogel can dynamically respond to changes in biomarker concentration and thereby dynamically change its volume (e.g., shrinking or swelling) in response to increased or decreased concentrations of available biomarker. As shown in FIG. 3, antibodies 304 can be added to a pre-polymerized hydrogel solution 302, and following polymerization, the antibodies 304 are positioned within the resultant biomarker sensitive hydrogel 306 so as to interact with biomarkers 310. In some instances, lithography or similar manufacturing methods can be used to first form a foundation of polymerized hydrogel—into which the antibodies are arranged—followed by polymerization of the remaining hydrogel.

As additionally illustrated in FIG. 3, the biomarker sensitive hydrogel 306 is configured to swell (e.g., as shown by swollen biomarker sensitive hydrogel 308) in response to interacting with additional biomarkers 310 and shrink (e.g., as shown in biomarker sensitive hydrogel 306) in response to a lower concentration of available biomarkers 310. Accordingly, the biomarker sensitive hydrogel 306 is configured to reach an equilibrium 312 between swollen and shrunken states based on the amount or concentration of biomarker 310 available to interact with the antibodies 304 within the biomarker sensitive hydrogel 306. In doing so, the biomarker sensitive hydrogel 306 acts as a biosensor for the amount or concentration of biomarker 310 in the vicinity of the biomarker sensitive hydrogel 306, and by determining the volume of the biomarker sensitive hydrogel 306, the amount or concentration of biomarker can be determined.

The possibility to tailor hydrogel responses to different analytes or stimuli has made hydrogels an attractive material for applications like drug delivery, sensing, actuation, and implants. Hydrogels, particularly biomarker sensitive hydrogels, are additionally attractive as a material for biosensing and as an implant due to its inherent biocompatibility, failure to elicit an immune response, and dynamic ability to correlate biomarker concentrations.

However, the ability to obtain a real-time, visual readout of hydrogel responses to analytes or other stimuli has proven problematic, particularly when the hydrogel is implanted in vivo. Noninvasive medical imaging techniques would be an ideal method to obtain a real-time, visual readout of hydrogel responses in vivo, but hydrogels are nearly invisible to most medical imaging devices—including ultrasound—making it difficult to determine any response of the hydrogel to surrounding analytes and/or stimuli. Thus, even though hydrogels represent a promising material for biomedical and biotechnological applications, their lack of visibility and concomitant lack of ability to be tracked in real time using current imaging devices and techniques renders their potential a moot point.

Identifying Changes in Biomarker Sensitive Hydrogels Using Ultrasound

Embodiments of the present disclosure enable the use of ultrasonic imaging to accurately measure changes in the volume and shape of biomarker sensitive hydrogels due to exposure to various biomarkers and thereby determine the concentration of biomarkers within an in vivo environment. Practicing the disclosed embodiments advantageously allows the use of existing, comparably cheap medical imaging technology to noninvasively obtain a real-time, visual readout of hydrogel swelling. Because biomarker sensitive hydrogels are biocompatible and essentially immunologically inert and because the specificity of biomarker sensitive hydrogels can be adapted to sense a variety of biomarkers, embodiments of the present disclosure advantageously enable the use and readout of long-term implants that can provide meaningful information about biomarker concentrations at an in vivo site. Further, the use of ultrasound to identify dimensional changes in a biomarker sensitive hydrogel placed within, for example, the human body is advantageous over optical sensing techniques, as ultrasound allows for a deeper reach into tissue.

Referring now to FIGS. 4A-4E, illustrated are exemplary biomarker sensitive hydrogels associated with a variety of ultrasound markers and/or contrast agents. The associated ultrasound markers and/or contrast agents provide at least a twofold benefit. First, the ultrasound markers and/or contrast agents associated with the biomarker sensitive hydrogel allow the biomarker sensitive hydrogel to be easier to locate in vivo and can even be used to define the general contour of the biomarker sensitive hydrogel with respect to surrounding structures. Second, the ultrasound markers and/or contrast agents associated with the biomarker sensitive hydrogel allow detection of dimensional changes within the biomarker sensitive hydrogel (e.g., swelling as a result of sensing a specified biomarker). In some embodiments, the addition of ultrasound markers and/or contrast agents to the biomarker sensitive hydrogel does not substantially interfere with or otherwise hinder the swelling and shrinking of the hydrogel in response to sensing an increase or decrease in the amount or concentration of specific biomarkers.

FIG. 4A illustrates an exemplary biomarker sensitive hydrogel 406a having a plurality of microbubbles 402 dispersed throughout the biomarker sensitive hydrogel 406a. In some embodiments, the microbubbles 402 are filled with gas, such as air. In some embodiments, the gas is a perfluorocarbon (e.g., a perfluoroalkane such as perfluoropropane). The microbubbles 402 are infused within the biomarker sensitive hydrogel 406a and act to reflect ultrasound waves emitted from an ultrasound transducer. Thus, the diffuse microbubbles 402 provide ultrasound contrast to a volume of space that is substantially coexistent with the biomarker sensitive hydrogel 406a, thereby allowing the hydrogel 406a to be more easily viewed using ultrasound. In some embodiments, one or more dimensional changes associated with the biomarker sensitive hydrogel 406a can be determined by tracking respective spatial locations of two or more microbubbles 402 or by comparing an average density of microbubbles within a given viewing window (e.g., as shown and described below with respect to FIG. 6).

In some embodiments, the diameter of the microbubbles is greater than 1 μm in diameter but less than 1 mm in diameter, greater than 10 μm in diameter but less than 1 mm in diameter, greater than 50 μm in diameter but less than 1 mm in diameter, greater than 100 μm in diameter but less than 1 mm in diameter, greater than 1 μm in diameter but less than 100 μm in diameter, greater than 1 μm in diameter but less than 50 μm in diameter, greater than 1 μm in diameter but less than 25 μm in diameter, or the diameter of the microbubbles is selected within a range defined by any of the foregoing upper and lower bounds.

FIG. 4B illustrates an exemplary biomarker sensitive hydrogel 406b having a plurality of barber pole stripes 404 disposed along the biomarker sensitive hydrogel 406b. In some embodiments, the barber pole stripes 404 include a metal film or wire (e.g., microwires or nanowires) disposed on top of, around, or inside the biomarker sensitive hydrogel 406b. The metal can be chosen from any sonically reflective metal that is at least somewhat biocompatible or non-toxic including, for example, gold, palladium, platinum, or silver. In some embodiments, the metal film or wire is helically disposed along or within the biomarker sensitive hydrogel 406b and is flexible along its helical axis such that volumetric changes of the biomarker sensitive hydrogel 406b cause elongation or constriction of the helix. Accordingly, volumetric changes within the biomarker sensitive hydrogel 406b can be tracked by measuring the distance between two or more barber pole stripes (e.g., two adjacent operable stripes).

In some embodiments, the hydrogel 406b is formed around the metal film or wire that comprises the plurality of barber pole stripes 404. For example, a helical metal film can be placed within a mold and a pre-polymerized solution of hydrogel can be poured over the helical metal film followed by polymerization of the hydrogel solution, thereby incorporating the helical metal film therein. In some embodiments, metal film or wire is added to the biomarker sensitive hydrogel 406b after the hydrogel is been manufactured. For example, the metal film or wire may be wound about a discrete portion of manufactured hydrogel to create the plurality of barber pole stripes 404. In some embodiments, the biomarker sensitive hydrogel 406b is manufactured using lithography, and the plurality of barber pole stripes 404 are generated during this process. In some embodiments, the biomarker sensitive hydrogel is fabricated, dried out and the plurality of barber pole stripes added by lithography based techniques for metallic thin film fabrication.

Referring now to FIG. 4C, illustrated is an exemplary biomarker sensitive hydrogel 406c having a sonically reflective and elastic sleeve 408 associated therewith. For example, the sleeve 408 may include an elastic material such as nitinol. Additionally, or alternatively, the sleeve 408 can be geometrically patterned (e.g., honeycombed or like chicken wire) to permit expansion or deformation in one or more spatial directions. The sonically reflective characteristics and elasticity of nitinol along with the defined geometric pattern of the sleeve 408 permit volumetric changes within the hydrogel 406c will also tracking such changes. For example, as the volume of the biomarker sensitive hydrogel 406c increases, the sleeve 408 elastically expands and distends one or more dimensions of the geometric shapes (e.g., the hexagonal honeycomb) that comprise the sleeve 408. These changes can be tracked and processed to determine an amount or concentration of biomarker.

Referring now to FIG. 4D, illustrated is an exemplary biomarker sensitive hydrogel 406d having a plurality of nanoparticles 410 overlain on the surface of the biomarker sensitive hydrogel 406d. It should be appreciated that FIG. 4D illustrates a planar front view of the biomarker sensitive hydrogel 406d, making it appear that the plurality of nanoparticles 410 are aligned in a single line or plane. In some embodiments, the plurality of nanoparticles are indeed aligned in a single line across the surface of the biomarker sensitive hydrogel. In other embodiments, the plurality of nanoparticles are dispersed across at least one surface of the biomarker sensitive hydrogel. In some embodiments, the plurality of nanoparticles are dispersed across more than one surface (or all surfaces) of the biomarker sensitive hydrogel. The plurality of nanoparticles 410 can include any sonically reflective nanoparticles, such as polystyrene nanoparticles, gold nanoparticles, silver nanoparticles, or combinations thereof. In some embodiments, the nanoparticles are equally distributed across the whole volume of the biomarker sensitive hydrogel.

Similar to the microbubbles of FIG. 4A, the sonically reflective nanoparticles 410 of FIG. 4D can be used to determine volumetric changes in the biomarker sensitive hydrogel 406d. For example, the distance between two or more nanoparticles 410 or an average density of nanoparticles on the surface of the biomarker sensitive hydrogel 406d taking at two time points can be used to identify volumetric changes in the associated biomarker sensitive hydrogel 406d. It should be appreciated that coating only a single surface of the hydrogel with sonically reflective nanoparticles may dictate or at least limit the angles at which the ultrasound can reveal the most informative data about the spatial relationships between nanoparticles on the surface of the hydrogel. For example, if the ultrasound was taken at an angle that yields the biomarker sensitive hydrogel 406d illustrated in FIG. 4D, less information can be accurately and consistently gleaned than if the ultrasound was taken at an angle orthogonal to the top surface of the biomarker sensitive hydrogel 406d.

Further, imaging only a single angle of the hydrogel yields a two-dimensional object from which three-dimensional volumetric data is extrapolated. In some embodiments, a second view of the hydrogel is obtained that is rotationally different than the first view to provide additional dimensional data for computing volumetric changes. In some embodiments, the two views are substantially orthogonal to one another. In some embodiments, more than two views are used (e.g., three views, four views, five views, six views, or more). It should be appreciated that in any of the foregoing and forthcoming embodiments where two-dimensional images are used to determine three-dimensional characteristics, it can be beneficial to obtain a second image that is taken in a different rotational plane (e.g., substantially orthogonal) than the first image.

Referring now to FIG. 4E, illustrated is an exemplary biomarker sensitive hydrogel 406e having a pair of contrast laden foci 412 disposed on opposite ends of the biomarker sensitive hydrogel 406e. In some embodiments, the foci 412 include any of the foregoing ultrasound markers and/or contrast agents disclosed in FIGS. 4A-4D. In some embodiments, the biomarker sensitive hydrogel 406e is extruded during manufacturing, and the initial N-terminal points of extrusion coincide with application of an ultrasound marker and/or contrast agent. In some embodiments, a volumetric change of the biomarker sensitive hydrogel 406e can be determined based on the difference between the foci 412.

In some embodiments, the biomarker sensitive hydrogel can be elongate in shape such that the width or diameter of the hydrogel is disproportionate to its length. In such embodiments, a volumetric change in the elongate hydrogel translates more noticeably into a change in length of the hydrogel. In some embodiments, the thickness to length ratio is no greater than 1/200:1 and/or no less than 1/20,000:1. In some embodiments, and subject to the foregoing, the elongate biomarker sensitive hydrogel can have a thickness greater than 5 µm, greater than 10 µm, greater than 20 µm, greater than 30 µm, greater than 40 µm, greater than 50 µm, greater than 70 µm, greater than 80 µm, greater than 90 µm, greater than 100 µm, greater than 150 µm, greater than 200 µm, less than 200 µm, less than 150 µm, less than 100 µm, less than 90 µm, less than 80 µm, less than 70 µm, less than 50 µm, less than 40 µm, less than 30 µm, less than 20 µm, less than 10 µm, or a thickness selected from a range consisting of any of the foregoing upper and lower bounds. For example, an elongate biomarker sensitive hydrogel can have a thickness between 10-100 µm. In some embodiments, and subject to the foregoing, an elongate biomarker sensitive hydrogel can have a length greater than 1 mm, greater than 2 mm, greater than 3 mm, dated and 4 mm, greater than 5 mm, greater than 7.5 mm, greater than 10 mm, greater than 12.5 mm, greater than 15 mm, greater than 20 mm, greater than 25 mm, less than 25 mm, less than 20 mm, less than 15 mm, less than 12.5 mm, less than 10 mm, less than 7.5 mm, less than 5 mm, less than 4 mm, less than 3 mm, less than 2 mm, less than 1 mm, or a length selected from a range consisting of any of the foregoing upper and lower bounds. For example, an elongate biomarker sensitive hydrogel can have a length between 2-20 mm.

Figure 5:
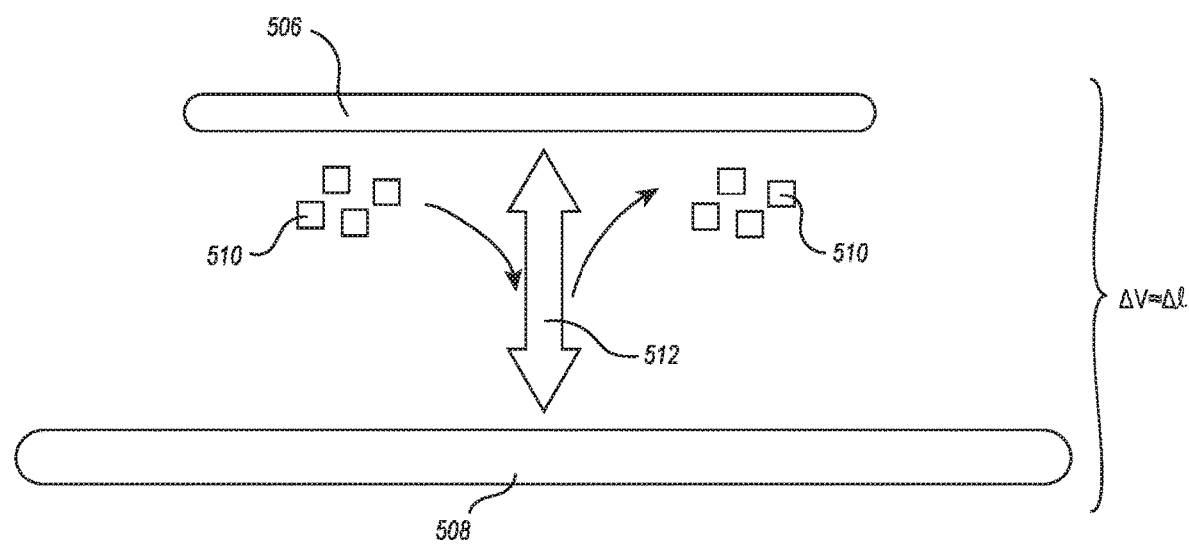
FIG. 5 illustrates the biomarker-dependent lengthening and shortening of elongate biomarker sensitive hydrogels.

For example, as shown in FIG. 5, an elongate biomarker sensitive hydrogel 506 can increase in volume upon interaction with a higher concentration one or more specific biomarkers 510, similar to those hydrogels described above. Similarly, the elongate biomarker sensitive hydrogel 506 can decrease in volume upon interaction with a lower concentration of one or more specific biomarkers 510.

Figure 6:
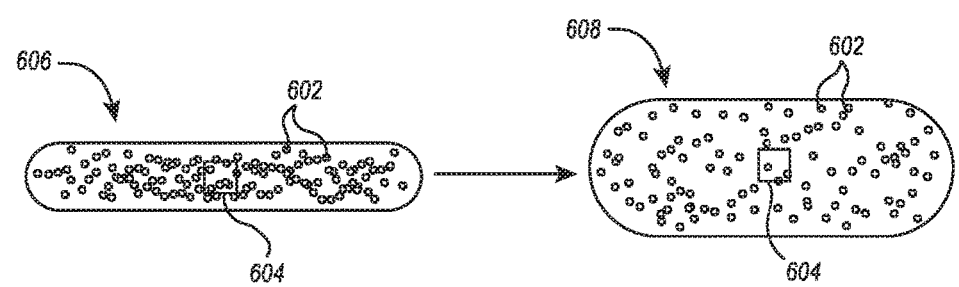
FIG. 6 illustrates a biomarker sensitive hydrogel in a shrunken state and a swollen state with a plurality of ultrasound markers or discreet contrast agents dispersed throughout and the measurable change in the average density or distance between the markers or discreet contrast agents between the shrunken and swollen states.

In some embodiments, the volumetric change in the elongate hydrogel is roughly proportional to a change in length, as shown in FIG. 6. In such embodiments, it may be beneficial to apply an ultrasound marker and/or contrast agent in the same or similar manner as illustrated by the biomarker sensitive hydrogel 406e of FIG. 4. That is, having two foci 412 positioned at opposite ends of an elongate biomarker sensitive hydrogel can quickly and easily identify changes in length, and in embodiments where volumetric changes are proportional to changes in length, a single image can be used to approximate or determine volumetric changes (and therefore an amount or concentration of biomarker). In some embodiments, this can save a significant amount of time and computing resources and can enable faster decision-making or increased availability of up-to-date information related to the amount or concentration of biomarker within an in vivo environment.

As alluded to above, an average density of ultrasound markers and/or contrast agents (e.g., microbubbles, sonically reflective nanoparticles, etc.) can be used to determine one or more dimensional changes of the hydrogel. FIG. 6 illustrates one method for determining the average density of ultrasound markers and/or contrast agents between two time points. As illustrated, an image of a biomarker sensitive hydrogel 606 having a plurality of discrete ultrasound markers and/or contrast agents 602 can be taken at a first time point. At a second time point, the biomarker sensitive hydrogel 606 has interacted with one or more predefined biomarkers, becoming a swollen biomarker sensitive hydrogel 608 having a plurality of discrete ultrasound markers and/or contrast agents 602. It should be noted that the total number of discrete ultrasound markers and/or contrast agent 602 remains the same between the two time points. However, the density of such discrete ultrasound markers and/or contrast agents 602 differs as the same number of discrete ultrasound markers and/or contrast agents 602 exist in a larger volume of space.

In some embodiments, and as depicted in FIG. 6, the density of discrete ultrasound markers and/or contrast agent 602 can be measured by overlaying a measurement window 604 of a predefined area onto images of the hydrogel 606, 608 taken at both time points. The number of discrete ultrasound markers and/or contrast agents 602 touching or within the area defined by the measurement window 604 can be counted, recorded or compared between the two time points. In some embodiments, an average number of discrete ultrasound markers and/or contrast agents 602 is determined based on sampling, at multiple locations, the number of discrete ultrasound markers and/or contrast agents 602 touching or within the area defined by the measurement window 604 and dividing by the total number of samples taken. These averages can be compared to determine volumetric changes (and therefore an amount or concentration of biomarker) between the biomarker sensitive hydrogel 606 and the swollen biomarker sensitive hydrogel 608.

Figure 7A:
FIG. 7A illustrates an exemplary ultrasound image depicting a biomarker sensitive hydrogel associated with gold nanoparticles.
Figure 7B:
FIG. 7B illustrates an exemplary ultrasound image depicting a plurality of nanowires associated with a biomarker sensitive hydrogel.

Referring now to FIGS. 7A and 7B, illustrated are exemplary ultrasound images depicting a biomarker sensitive hydrogel being viewed using standard ultrasound equipment. As shown in FIG. 7A, for example, a biomarker sensitive hydrogel associated with gold nanoparticles can be viewed using a Siemens® 18L6 HD transducer emitting at 17.00 MHz, well within diagnostic frequencies. Similarly, as shown in FIG. 7B, differently spaced nanowires associated with a biomarker sensitive hydrogel can be viewed using a Siemens® 18L6 HD transducer emitting at 17.00 MHz. It should be appreciated that although not shown, the different ultrasound markers and/or contrast agents discussed and illustrated in FIGS. 4A-4E can also enable a biomarker sensitive hydrogel to be viewed using ultrasound at a clinically relevant frequencies.

Systems for Identifying In Vivo Changes of Biomarker Sensitive Hydrogels

Figure 8:
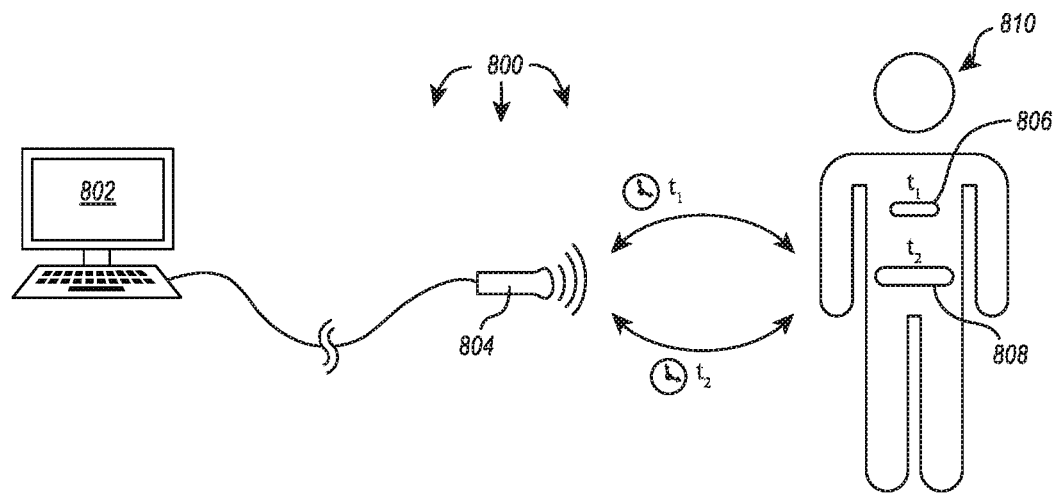
FIG. 8 is a diagram that illustrates an exemplary system for identifying one or more changes in a biomarker sensitive hydrogel positioned within an in vivo environment.
Figure 9:
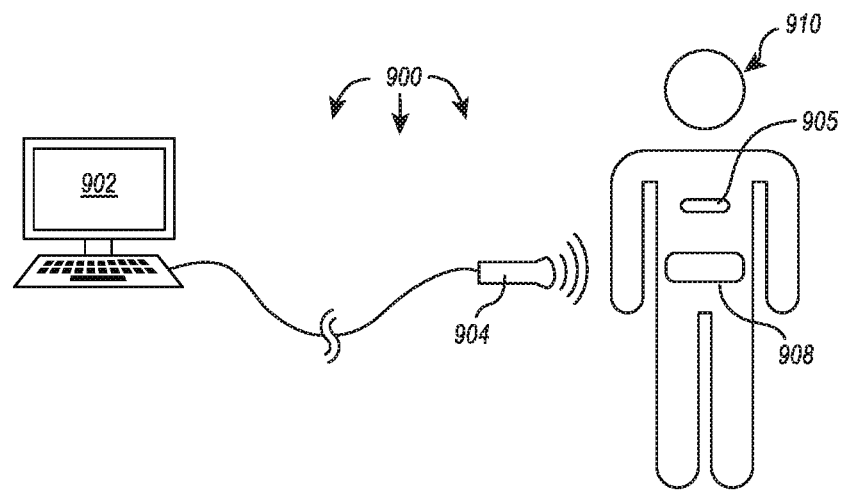
FIG. 9 is a diagram that illustrates another exemplary system for identifying one or more changes in a biomarker sensitive hydrogel positioned within an in vivo environment.
Figure 10:
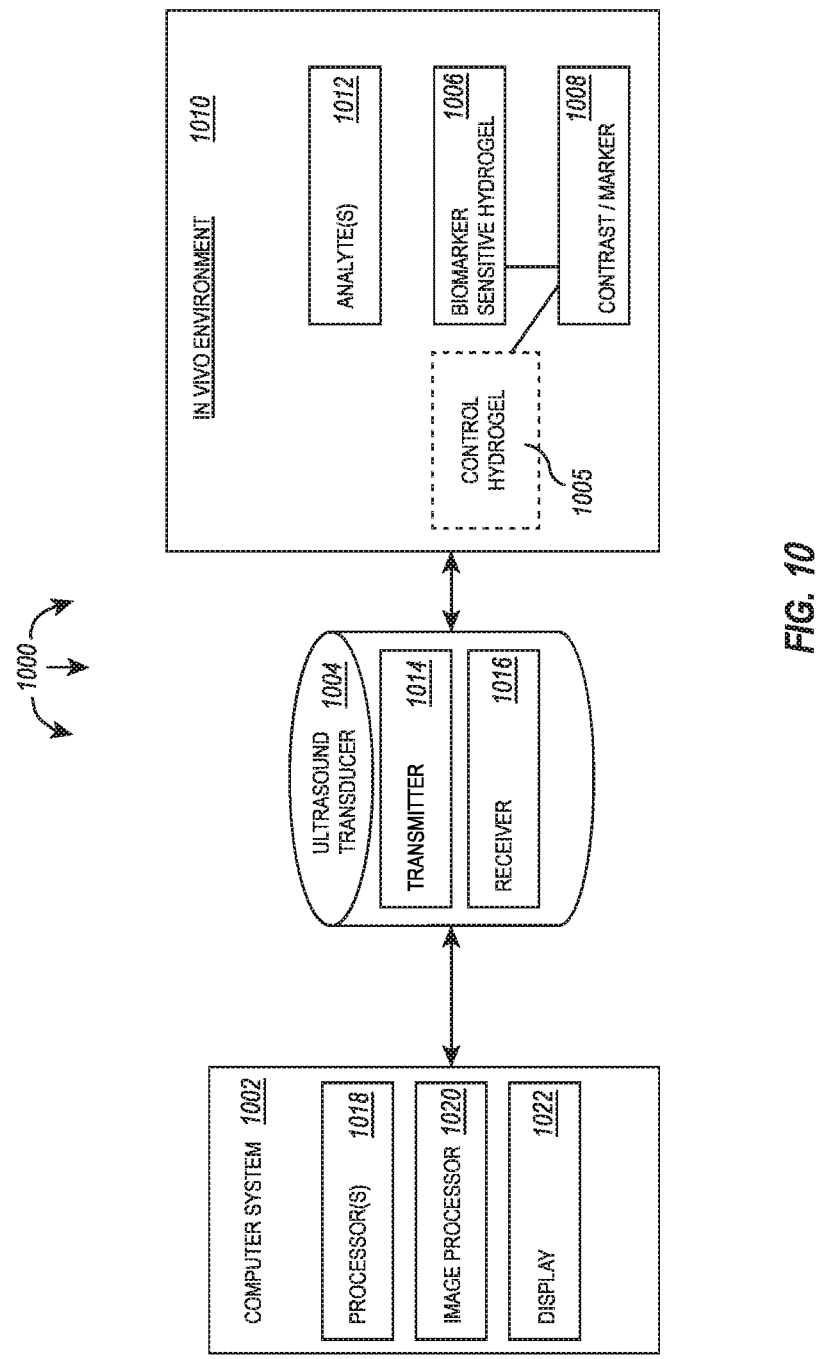
FIG. 10 illustrates an exemplary system for identifying one or more changes in a biomarker sensitive hydrogel positioned within an in vivo environment.

Referring now to FIGS. 8-10, illustrated are systems for identifying one or more changes in a biomarker sensitive hydrogel positioned within an in vivo environment (e.g., inside the human body). FIG. 8, for example illustrates a diagram of an exemplary system 800 for identifying changes in a biomarker sensitive hydrogel 806, 808 over time. The system 800 includes a biomarker sensitive hydrogel positioned within an in vivo environment 810, an ultrasound transducer 804, and a computing system 802 in electrical communication with the ultrasound transducer 804. At a first time, the ultrasound transducer 804 locates the biomarker sensitive hydrogel 806 within the in vivo environment 810. In some embodiments, the biomarker sensitive hydrogel 806 is associated with an ultrasound marker and/or contrast agent (as described above), which may assist in locating the biomarker sensitive hydrogel 806 within the in vivo environment 810. The computing system 802 can identify and/or record one or more characteristics the biomarker sensitive hydrogel 806 at the first time point ($t_1$). In some implementations, and for the purposes of FIG. 8, the biomarker sensitive hydrogel 806 can reach a physiologic equilibrium with one or more stimuli (e.g., pH, osmolarity, temperature, etc.) and the basal levels (or non-existence) of biomarker within the in vivo system 810 prior to identifying and/or recording one or more characteristics of the biomarker sensitive hydrogel 806 at the first time point ($t_1$).

At a second time point ($t_2$)—the second time point coming chronologically after the first time point ($t_1$)—the ultrasound transducer 804 again locates biomarker sensitive hydrogel 808 in the in vivo environment 810, and the computing system 802 identifies and/or records one or more updated characteristics of the biomarker sensitive hydrogel 808. As shown in FIG. 8, the biomarker sensitive hydrogel 808 is swollen compared to the biomarker sensitive hydrogel 806 at the first time point ($t_1$). In some embodiments, the second time point ($t_2$) can occur during or after an event that causes an increase in the amount or concentration of the specific biomarker. The increase in the amount or concentration of the specific biomarker can cause swelling of the biomarker sensitive hydrogel 806 (similar to that shown in FIG. 8).

The system 900 of FIG. 9 is similar in many respects to the system 800 of FIG. 8. For example, the system 900 includes an ultrasound transducer 904 in electronic communication with a computer system 902. The ultrasound transducer 904 is configured to transmit and receive ultrasonic signals for identifying and/or monitoring a biomarker sensitive hydrogel 908 within the in vivo environment 910 and for identifying one or more characteristics of the biomarker sensitive hydrogel 908. As opposed to system 800 of FIG. 8, which relied on implanting a single biomarker sensitive hydrogel 806, 808 and identifying differences over time, system 900 of FIG. 9 utilizes a control hydrogel 905 to establish a baseline of comparison for one or more characteristics of the biomarker sensitive hydrogel 908. In some embodiments, the control hydrogel 905 is made of the same or substantially the same polymerized material but is configured not to interact with the predefined biomarker associated with the biomarker sensitive hydrogel 908. In some embodiments, the control hydrogel 905 may still be capable of swelling in response to environmental stimuli such as pH and osmolarity so that the control hydrogel 905 can more accurately represent a baseline swelling or other dimensional or material properties that should be similarly exhibited by the biomarker sensitive hydrogel 908. Accordingly, at any given time the differences in one or more characteristics between the biomarker sensitive hydrogel 908 and the control hydrogel 905 are indicative and/or caused by the biomarker sensitive hydrogel 908 interacting with one or more predefined biomarkers.

In some embodiments, the control hydrogel 905 includes one or more of the same ultrasound markers and/or contrast agents as the biomarker sensitive hydrogel 908. In some embodiments, the control hydrogel 905 and the biomarker sensitive hydrogel 908 include different ultrasound markers and/or contrast agents. In still further embodiments, the control hydrogel 905 and the biomarker sensitive hydrogel 908 may each have specificity for a different biomarker. For example, the control hydrogel 905 may be sensitive for a biomarker that should not be present within the in vivo environment (e.g., peptidoglycan, viral capsid proteins, or other indications of infection at a typically sterile site), thereby acting as a control in almost every situation but simultaneously having an alarm function for the presence of potentially deleterious biomarkers.

Although the in vivo environment 810 is generically depicted in FIGS. 8 and 9 as being within the human body, it should be appreciated that the in vivo environment can include any number or types of locations within the human body. For example, the biomarker sensitive hydrogel can be placed within the bloodstream to identify an amount or concentration of thrombin, clotting cascade factors, interleukins, cytokines, chemokines, C-reactive protein, or other biomarker associated with clotting processes and/or pro-inflammatory/anti-inflammatory responses. Such a biomarker sensitive hydrogel can be useful, for example, to monitor healing of the patient after trauma or surgery, and because the hydrogel can be read out using ultrasound techniques, such information can be obtained on demand and noninvasively.

Other implementations within the blood include monitoring a biomarker sensitive hydrogel that is specific for peptidoglycan, mycolic acid, viral capsid proteins, or other bacterial and/or viral specific antigens as a means of noninvasively monitoring the patient for bacteremia, viremia, or other blood-based infection. This can increase the reaction time of attending medical professionals to potentially life-threatening conditions, particularly in immunocompromised patients, so that the infection can be caught and treated early on where the prognosis for recovery is best. This can be particularly impactful, for example, in patients at risk for septicemia, where survival rates are inversely and exponentially correlated with the number of hours the patient is septicemic.

Yet other implementations within the blood include monitoring a biomarker sensitive hydrogel within a diabetic patient or pregnant individual where the hydrogel is specific for blood glucose or insulin. The hydrogel can thereby act as a mechanism by which the individual can quickly and noninvasively monitor their blood glucose levels and/or insulin levels to more effectively and efficiently manage and/or track their condition.

Still yet other implementations within the blood include monitoring a biomarker sensitive hydrogel within patients under general anesthesia. The hydrogel can be specific for one or more active components of the anesthesia or metabolic derivatives thereof, allowing an anesthesiologist or other healthcare provider to more accurately monitor the amount or concentration of anesthesia in the patient's bloodstream and to adjust one or more drugs according to the patient's individual ability to metabolize and/or filter the drugs from their system. A similar approach can be adapted for use in patients prescribed restricted drugs or drugs associated with a high incidence of abuse and/or addiction (e.g., opioids, amphetamines, etc.). The amount or concentration of the prescribed medication can be monitored to ensure compliance and/or to prevent abuse.

In some implementations, the in vivo environment for placement and monitoring of a biomarker sensitive hydrogel can include the bladder (e.g., for monitoring biomarkers correlating with organ failure, infection, eating disorders, preeclampsia, etc.), the vagina (e.g., for monitoring pH, hormones, biomarkers associated with pregnancy, etc.), liver, kidney, or deep tissue area.

It should be appreciated that while the foregoing disclosure has focused mainly on humans, the same or analogous biomarker sensitive hydrogels can be used within in vivo environments of nonhuman animals.

Additionally, or alternatively, implementations can include the use of analyte sensitive hydrogels within environmental locations. This may be particularly advantageous when monitoring, for example, water lines for the presence of pollutants (e.g., toxic metals, known carcinogens, etc.), microbial contamination, or additives (e.g., fluoride). Multiple analyte sensitive hydrogels can be placed at critical points within a supply line and quickly and noninvasively monitored using ultrasound. In some implementations, strategic placement of analyte sensitive hydrogels within environmental locations (e.g., along a water way or within a water line) can assist in and/or expedite identification of contaminating source or other issue. In some implementations, the analyte sensitive hydrogel can be multifaceted such that it will swell in response to interaction with any one of the plurality of analytes. This may be advantageous, for example, in situations where the analyte sensitive hydrogel identifies pollutants or contaminants, any of which alone may be cause for concern and/or the confluence of all should be below the prescribed threshold. In this way, a single hydrogel can be placed and monitored as opposed to deploying a plurality of individually specific analyte sensitive hydrogels to accomplish the same or similar purpose. As such, the foregoing implementations can save time and provide a more effective use of resources.

Referring now to FIG. 10, illustrated is an exemplary system 1000 for identifying one or more changes in a biomarker sensitive hydrogel 1006 that is positioned within an in vivo environment 1010. As illustrated, the system 1000 includes a computer system 1002 in communication with an ultrasound transducer 1004 which can communicate with the in vivo environment 1010. From the perspective of the computer system 1002, location data and/or data associated with characteristics of a biomarker sensitive hydrogel 1006 and optionally the control hydrogel 1005 are received through ultrasound transducer 1004. At the processor 1018, the received data is analyzed to determine changes, if any, in the characteristics of the biomarker sensitive hydrogel 1006 between successive time points and/or between analogous characteristics received for the control hydrogel 1005. Any changes identified can be used to determine one or more dimensional changes of the biomarker sensitive hydrogel 1006, which in turn can be used to determine an amount or concentration of analyte(s) 1012 within the in vivo environment 1010. The computer system 1002 can additionally process image data received from the ultrasound transducer 1004 using image processor 1020 and display the processed image data at display 1022. In some embodiments, the computer system 1002 can display any of the amount or concentration of analyte 1012, the determined dimensional changes of the biomarker sensitive hydrogel 1006, and/or the identified characteristics of biomarker sensitive hydrogel 1006 and/or control hydrogel 1005.

Hydrogel Resonator Sheets

In some implementations, it may be useful to know and/or have access to information regarding site-specific concentrations of biomarkers, particularly during procedures that are already utilizing an ultrasound transducer to acquire image data. However, current ultrasound transducers lack the resolution or ability to identify individual biomarkers using the transducer alone. Embodiments of the present disclosure include hydrogel resonator sheets that can be adapted for use on a chip-based implant (as shown, for example, in FIGS. 12A and 12B) or as part of a protective sleeve for ultrasound transducers (as shown, for example, in FIGS. 13-15). The hydrogel resonator sheets disclosed herein provide site-specific information regarding an amount or concentration of a biomarker and can do so, in some embodiments, independently from the use of an ultrasound marker and/or contrast agent.

Figure 11:
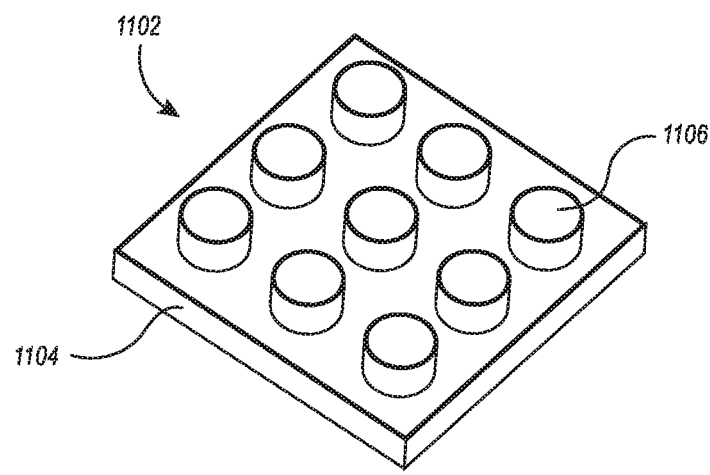
FIG. 11 illustrates an exemplary hydrogel resonator sheet.

FIG. 11 illustrates an exemplary hydrogel resonator sheet 1102, which includes a hydrogel base plate 1104 and a biomarker sensitive hydrogel arranged in an array of resonators 1106 that undergo one or more physical changes (e.g., swelling) in response to interacting with one or more predefined biomarkers. In some embodiments, the functional aspects of the hydrogel contained within the hydrogel resonator sheet 1102 is the same and/or substantially similar to the hydrogels disclosed above. For example, the biomarker sensitive hydrogel used to form the resonators 1106 can undergo volume changes in response to association with one or more predefined biomarkers, particularly in response to association with a higher concentration of the one or more predefined biomarkers. As above, the biomarker sensitive hydrogel used to form the resonators 1106 can also decrease in volume in response to association with lower concentrations of the one or more biomarkers.

In some embodiments, the resonators 1106 absorb certain ultrasound frequency bands. Accordingly, at some frequencies, particularly where the main mode or resonant frequency of the resonators 1106 is located, resonators 1106 can cause a signal reduction or "dip" in the intensity of the received ultrasonic waves. The signal reduction is a result of transmitted waves being absorbed by the resonators 1106 instead of being reflected back to the transducer. This phenomenon occurs to a large extent at the main mode (the resonant frequency), and to a lesser extent at higher order harmonic frequencies (e.g., $2^{nd}$ and $3^{rd}$ harmonic frequencies), and is dependent upon the volume of the resonator 1106. It should be appreciated that in some embodiments the hydrogel array includes an array of sensors, and therefore, the resultant main mode observed is a collective effect achieved by the coupling of the main modes of all the resonators in the array. Further, the dimensions of the resonator can be tailored to a desired frequency range. Accordingly, as the resonator 1106, which is comprised of a biomarker sensitive hydrogel, swells or shrinks in response to interactions with predefined biomarkers, the volume of the resonator 1106 increases and decreases. The increasing or decreasing spatial volume (and accompanying change in material properties) of the resonator 1106 causes a shift in the resonant frequency of the resonator 1106.

Figure 21:
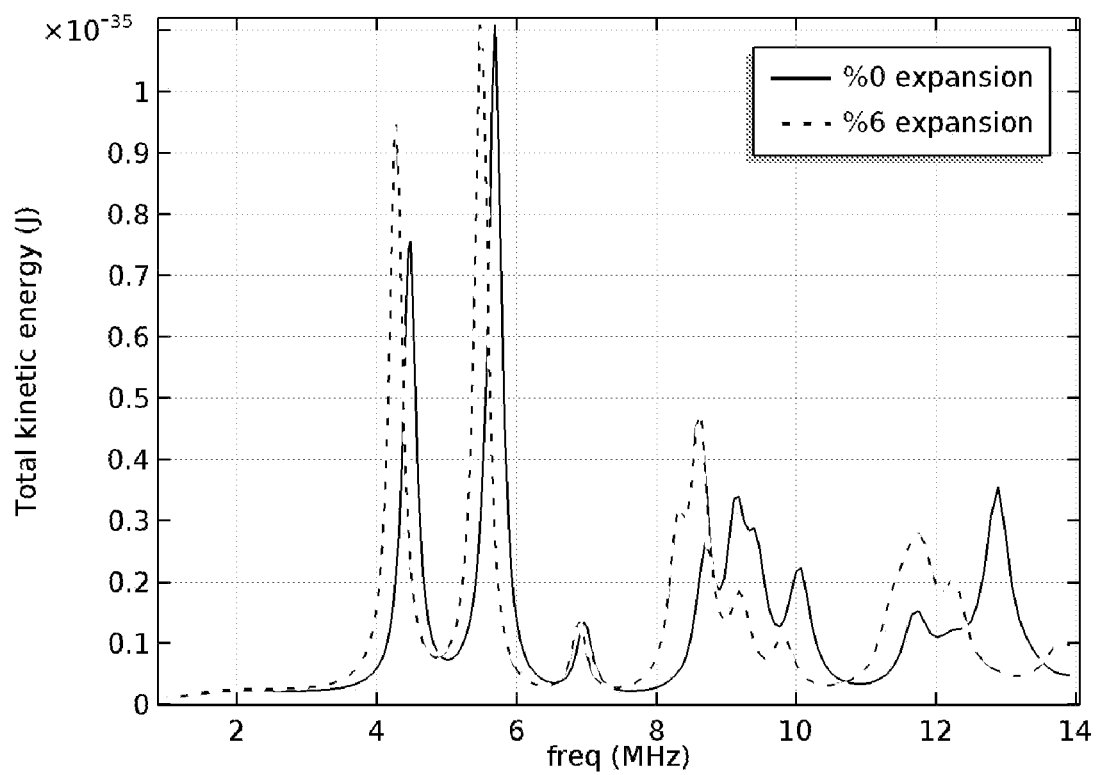
FIG. 21 is a graph illustrating a frequency shift in a hydrogel resonator sheet as it changes dimensional or material characteristics.

Such a phenomenon is illustrated, for example in FIG. 21. As shown, a 0% expansion of the hydrogel comprising at least a portion of the resonator sheet has a defined kinetic energy profile along a frequency spectrum. Upon expansion (e.g., as a result of interaction with the hydrogel-specific stimulus/stimuli), the resonant frequency of the hydrogel shifts. The frequency shift of a 6% expansion of the hydrogel is shown in FIG. 21. In some embodiments, the frequency shift along a range of hydrogel expansion can be determined ahead of time, and by comparing the known frequency shift given a particular expanded state with the observed frequency shift, the degree of volumetric change can be determined. In some embodiments, comparing a known volumetric change resulting from interaction with a defined concentration of stimulus (e.g., biomarker) with the observed or determined volumetric change in the hydrogel sheet, the concentration of stimulus can be extrapolated.

By identifying a first frequency that corresponds to the resonator's 1106 main mode (e.g., by scanning through a plurality of frequencies to find a significant signal reduction), changes in the main mode can be tracked (e.g., by following the frequency shift in the signal reduction). The tracked frequency changes in the main mode can be directly correlated to a volumetric change of the resonators 1106, and upon determining the volumetric change of the resonators 1106, a corresponding amount or concentration of biomarker can be determined. In this way, the disclosed hydrogel resonator sheets can indirectly utilize ultrasound to determine an amount or concentration of a biomarker within an in vivo environment.

With continued reference to FIG. 11, the hydrogel baseplate can, in some embodiments, contribute to frequency absorption at the main mode. Additionally, or alternatively, the hydrogel baseplate can provide leverage and connectivity for manipulating the array of resonators both during manufacturing and/or molding as well as during manipulation of the hydrogel resonator sheet onto sensor arrays or other platforms. In some embodiments, the baseplate can be made from a different material (e.g., polyimide, silicone, etc.) to facilitate handling. In some embodiments, it is advantageous to make the baseplate from hydrogel because of ease of fabrication and because it likely does not obstruct the ultrasound waves outside the resonance band.

Figure 12A:
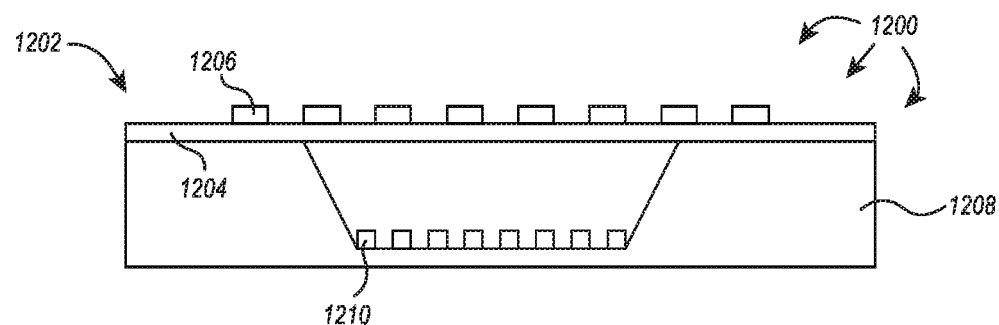
FIG. 12A illustrates a front view of a chip-based biomarker sensor incorporating a hydrogel resonator sheet.
Figure 12B:
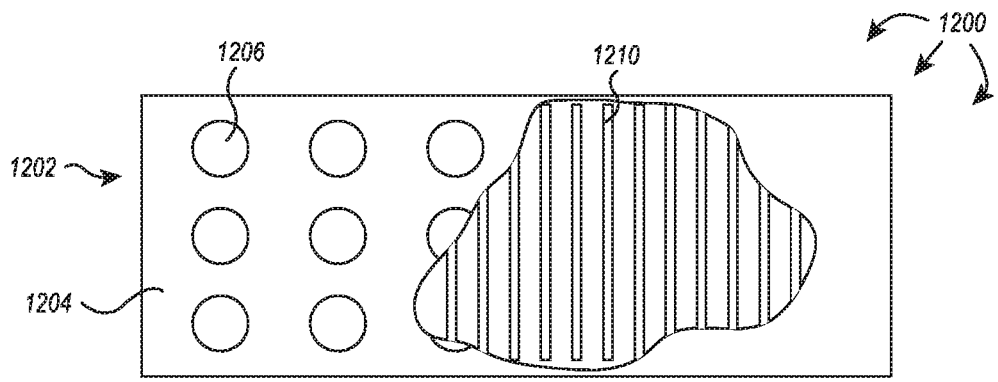
FIG. 12B illustrates a top, partial cut away view of the chip-based sensor of FIG. 12A.

For example, as shown in FIGS. 12A and 12B, a sensor array 1200 can include a hydrogel resonator sheet 1202 attached to a chip 1208. In some embodiments, the chip 1208 is a silicone chip and includes a contrast structure 1210 positioned beneath the hydrogel resonator sheet 1202. The contrast structure 1210 can, in some embodiments, provide a spatially rigid reference for comparing swelling and/or shrinkage of the hydrogel resonator sheet (or components thereof) and which can additionally be seen using ultrasound. For example, the contrast structure 1210 can include a plurality of evenly spaced ridges, which in some embodiments can be a metal or other sonically reflective material, to locate the hydrogel and to provide a contrast feature that can be used to observe the loss of contrast (=signal/intensity) to find the signal dip. The contrast structure is superior, in some embodiments, than using arbitrary body tissue to observe a loss of contrast. This can be used to identify shifts in the resonance frequency of the hydrogel and thereby determine volumetric changes in the hydrogel (and therefore an amount or concentration of biomarker).

Implementations of the chip-based sensor shown in FIGS. 12A and 12B include in vivo implantation for any of the purposes described above and can additionally include placement within the environment, also as described above. Advantageously, the sensor can provide additional durability and can also be incorporated more rigidly into existing (or slightly adapted) sensors and/or implants.

Ultrasound Resonator Sleeves

Ultrasound transducers can be used internally to, for example, obtain different angled views of an internal structure and/or to provide better resolution images. Ultrasound transducers can also be used internally to guide minimally invasive procedures, including minimally invasive surgical procedures. In a very common procedure for pregnant women, an ultrasound transducer is positioned within the vaginal canal so the physician can get a proper angled and/or better image of various internal structures, such as, for example, the cervix, the uterus, the placenta, or the fetus. Before the procedure, the ultrasound transducer is often placed within a protective sleeve—both to protect the patient from possible infection and to protect the ultrasound transducer from potential contamination.

Figure 13:
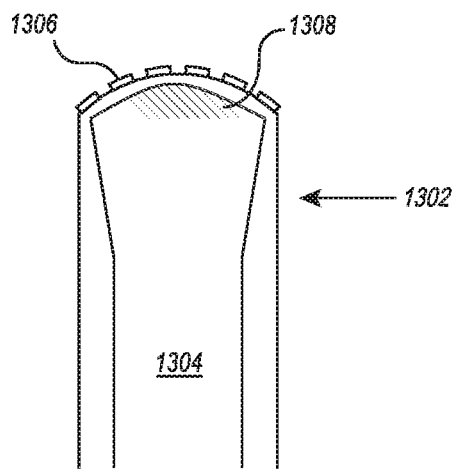
FIG. 13 illustrates an exemplary ultrasound transducer sleeve associated with a hydrogel resonator sheet, as applied to an ultrasound transducer.

As illustrated in FIG. 13, and ultrasound transducer 1304 can be associated with a sleeve 1302 in a similar fashion to that described above. However, the sleeve 1302 additionally includes a plurality of resonators 1306 that are the same as and/or substantially similar to the resonator structures 1106, 1206 described above. In some embodiments, a gel acoustic coupling 1308 can be applied between the ultrasound transducer 1304 and the sleeve 1302, particularly that portion of the ultrasound transducer 1304 beneath the resonators 1306. The gel acoustic coupling 1308 can, for example, provide a medium through which ultrasound frequencies can be transmitted and received with higher fidelity.

Figure 14:
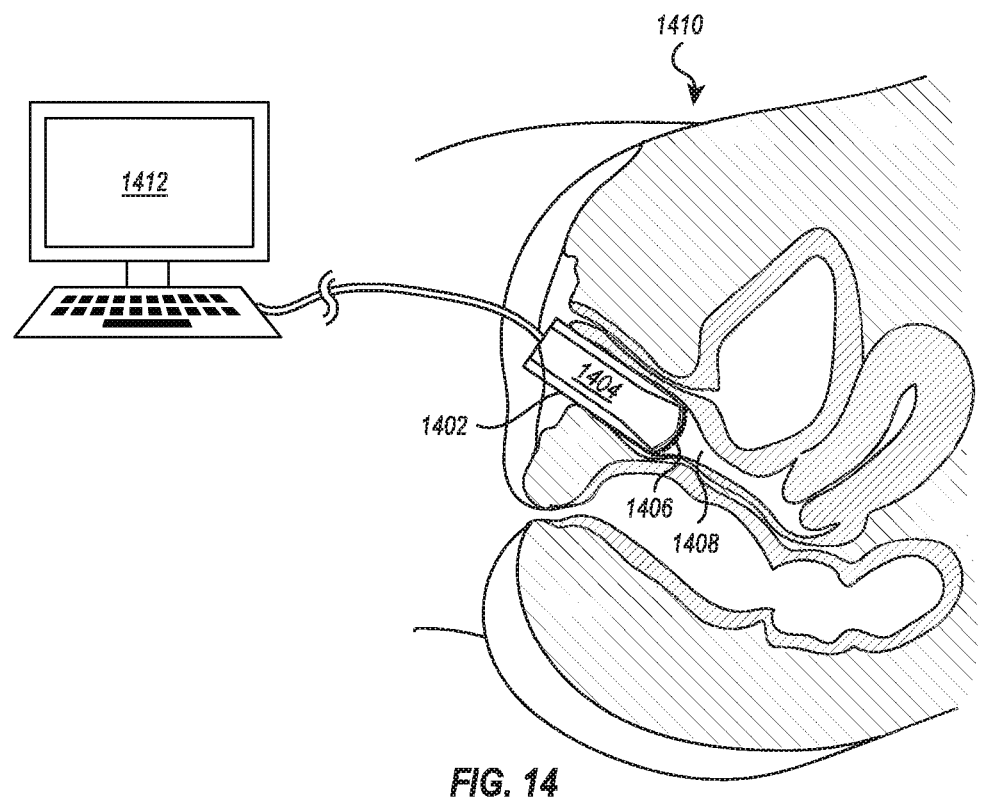
FIG. 14 illustrates an intravaginal ultrasound using the sleeve-associated ultrasound transducer as an exemplary in vivo implementation of the sleeve-associated ultrasound transducer of FIG. 13.
Figure 15A:
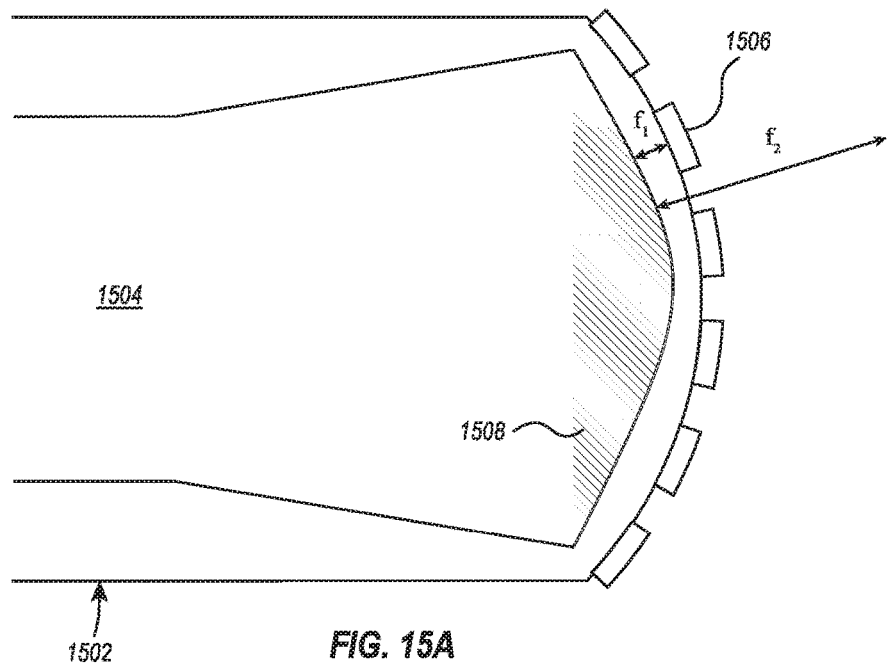
FIG. 15A illustrates a close up view of the sleeve-associated ultrasound transducer of FIG. 13 emitting and receiving a plurality of ultrasonic frequencies.
Figure 15B:
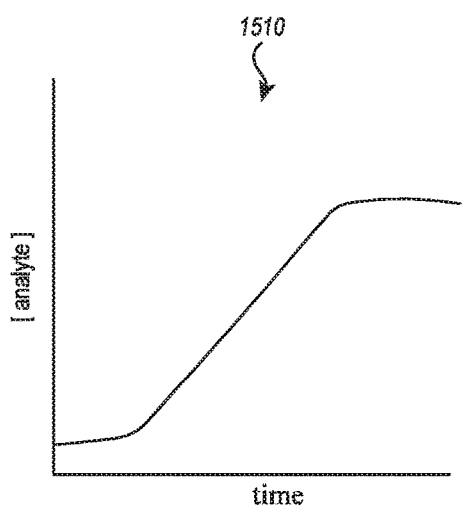
FIG. 15B illustrates an exemplary graphical representation of a possible analyte concentration over time, as determined from monitoring the first frequency illustrated in FIG. 15A.
Figure 15C:
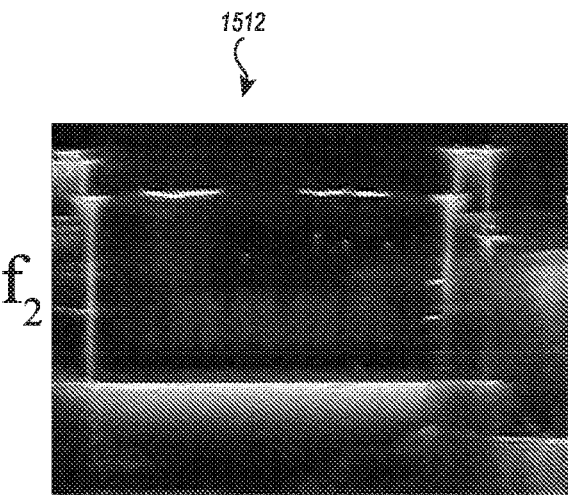
FIG. 15C illustrates an exemplary ultrasound image obtained by processing data received from a frequency outside the resonator resonance frequencies illustrated in FIG. 15A.

As shown in FIG. 14, the ultrasound transducer 1404 and associated sleeve 1402 can be inserted into an in vivo environment 1410 (particularly the vaginal canal 1408) where the ultrasound transducer 1404 can be used to both image the in vivo environments 1410 as well as monitor one or more biomarkers within the in vivo environment 1410. This is perhaps better illustrated in FIG. 15A, where the ultrasound transducer 1504 is shown as emitting at least two ultrasound frequencies $f_1$ and $f_2$. The first frequency ($f_1$) is directed to the frequency of the main mode of the resonator 1506, and the second frequency ($f_2$) can be directed to any other frequency used for ultrasound imaging that is not the main mode of the resonator 1506.

Accordingly, the ultrasound transducer 1504 can perform to simultaneous functions. The ultrasound transducer 1504 can function as an imaging device by transmitting and receiving a frequency (or frequencies) other than the frequency associated with the main mode of the resonators 1506. The data received from this transmission and reception frequencies can then be processed into one or more images 1512. The ultrasound transducer 1504 can additionally perform the function of monitoring the frequency of the main mode associated with the resonators 1506 and tracking any changes or shifts in the frequency of the main mode or other significant features of the frequency spectrum (e.g., higher modes can be advantageous for higher sensitivity). These data can be processed to determine a volumetric change in the resonators 1506 and therefore an amount or concentration biomarker specific to the hydrogel comprising the resonators 1506 (as shown in graph 1510). It should be appreciated that some embodiments, the shifting main mode frequency of the resonators 1506 can indirectly be used to graph a change in concentration of analyte (e.g., a biomarker) over time.

The aforementioned processing steps can be performed, for example, by a computer system. For example, the computer system 1412 that is in electrical communication with ultrasound transducer 1404 of FIG. 14 can perform the processing steps to both display an ultrasound image and determine a biomarker concentration. In some embodiments, the computer system is a portable computer system or controller that is both electrically and physically coupled to the ultrasound transducer. In some embodiments, the computer system is an electronic mobile device (e.g., a tablet or smart phone) that either communicates directly with the ultrasound transducer or communicates with the ultrasound transducer (e.g., receiving information) through a cloud-based system. In other embodiments, the computer system is a desktop or laptop computer in electrical communication with the ultrasound transducer.

Figure 16:
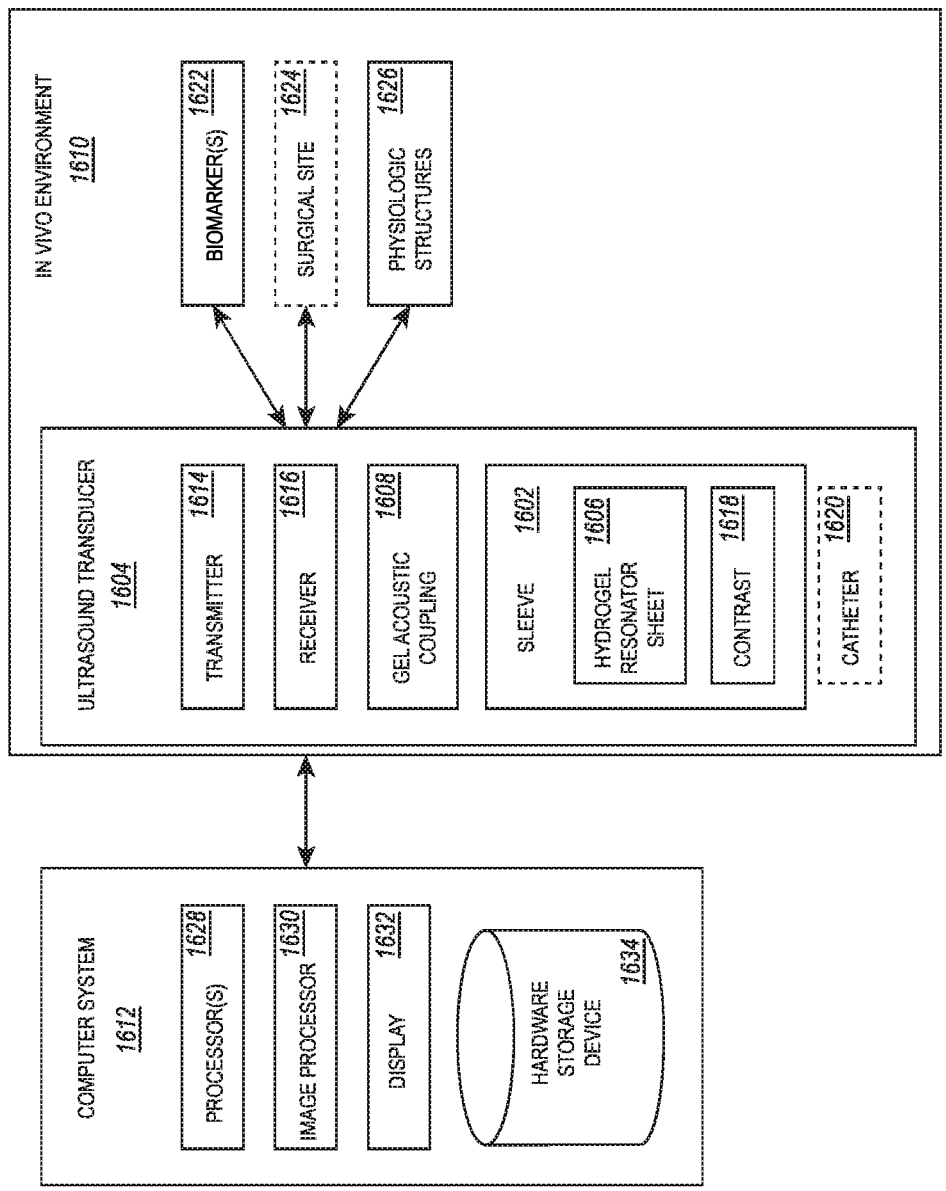
FIG. 16 illustrates an exemplary system for detecting a concentration of one or more biomarkers within an in vivo environment.

Illustrated in FIG. 16 is a system for detecting a concentration of one or more biomarkers 1622 within an in vivo environment 1610. The system of FIG. 16 includes a computer system 1612 and an ultrasound transducer 1604 coupled to a sleeve 1602. The ultrasound transducer 1604 and sleeve 1602 are provided within an in vivo environment 1610 and through transmitters 1614 and receiver 1616, the ultrasound transducer 1604 can obtain information related to physiologic structures 1626 (e.g., imaging data) and biomarkers 1622 (e.g., resonance frequency data and shifts associated therewith). This information can be received by the computer system 1612 where the processors 1628 determine a volumetric change of at least portions of the hydrogel resonator sheet 1606 associated with the sleeve 1602 based on one or more shifts in the main mode or resonant frequency of the hydrogel resonator sheet 1606. Based upon the volumetric change of at least portions of the hydrogel resonator sheet 1606, the processors 1628 can determine an amount or concentration of biomarker 1622 within the in vivo environment 1610. Any of the foregoing data—both received and determined—can be stored within hardware storage device 1634.

Additionally, the image processor 1630 of the computer system 1612 can receive the image data and generate one or more ultrasound images therefrom. The generated ultrasound images can be sent to and displayed on display 1632 and/or stored within hardware stores device 1634.

In some embodiments, the ultrasound transducer 1604 and sleeve 1602 (and components associated therewith) can be sized and shaped to fit within a catheter 1620 for transit to a surgical site 1624. In some embodiments, information received at the ultrasound transducer can be transmitted in real time to the computer system 1612 where the data can provide relevant information to the medical service provider regarding the surgical site 1624 or biomarker 1622 associated therewith. As an illustrative example, an ultrasound transducer can be passed through a catheter to a distant surgical site where the sleeve associated with the ultrasound transducer includes resonators on the hydrogel resonator sheet that comprise a biomarker sensitive hydrogel specific to thrombin. As the surgery progresses, and the local concentrations of thrombin increase, these data can be obtained using ultrasound (as described above) and further elucidated using computer 1612. The real time or near real time thrombin concentration at the surgical site can be presented to the medical professional performing the surgery (e.g., at the display of the computer system). In some embodiments, the catheter-based ultrasound transducer can be associated with a sleeve having disposed thereon a biomarker sensitive hydrogel arranged within an array of resonators, and as described above, using ultrasound and the biomarker sensitive hydrogel, an amount or concentration of biomarker can be detected at or near the location of the ultrasound transducer. As a particular non-limiting example, the foregoing can be used in cardiac surgery, such as arterial fibrillation ablation surgery.

The resonator sheets described above can be incorporated into the sensors (as in FIGS. 12A and 12B) and/or sleeves (as in FIGS. 13-15A) as described. In some embodiments, however, alternative resonator arrays can be incorporated into the foregoing. For example, the alternative array structures depicted in FIGS. 17A and 17B can be incorporated within embodiments disclosed herein to, for example, increase transmission in certain frequency bands and/or enable harmonic suppression. Importantly, the resonance frequency of resonators depends on the mechanical properties they exhibit in addition to the geometry of the resonators independently and collectively. Because hydrogels can experience a change in mechanical properties and volume (which are usually interconnected) when exposed to a stimulus or analyte, a sheet of stimuli responsive hydrogel resonators can be used together with ultrasound as a readout mechanism to create an analyte sensor. The resonators have different transmission and reflection values along a frequency range. In some embodiments, it is expected that the reflection of the hydrogel sheets will be low and ineffectual for detection. The detected dip in the signal is due in large part to the fact that these sheets absorb strongly at their resonance frequencies and do not absorb much at other frequency bands. The ultrasonic signal usually needs to be reflected from something else (e.g., tissue, contrast structure, etc.) in order to reach the transducer again. In many pulse echo modes of commercial ultrasound equipment, the waves also need to pass the resonators twice, thereby increasing their effect. Therefore, the ultrasonic waves produced by an actuator could be recorded after passing through or scattering from these resonators. The changes in resonance frequency of the structure changes the frequency response which could be quantified and translated into an amount or concentration of analyte.

As shown in FIG. 17A, one structure for the hydrogel resonator array is a repeated pattern of cylindrical ultrasonic resonators, each resonator having a diameter of 3.5 µm. In some embodiments, each resonator has a diameter greater than 1 µm, greater than 2 µm, greater than 3 µm, greater than 4 µm, greater than 5 µm, greater than 7.5 µm, greater than 10 µm, greater than 15 µm, greater than 20 µm, less than 20 µm, less than 15 µm, less than 12.5 µm, less than 10 µm, less than 7.5 µm, less than 5 µm, less than 4 µm, less than 3 µm, less than 2 µm, less than 1 µm, or a diameter chosen from a range of diameters having a lower and upper bound selected from the foregoing. The illustrated array includes a main resonance peak (i.e., a main mode) and several other smaller peaks. At a resonance frequency, the hydrogel sheet absorbs more wave intensity and transmits less. Having a fewer number of resonance peaks can facilitate the detection of the main peak more easily and/or quickly. This, in turn, makes tracking the shifting main mode easier. Also, this can be used to clear more frequency bands, the cleared frequency bands being able to be used for conventional ultrasound imaging.

As shown in FIG. 17B, an additional structure for a hydrogel resonator array is depicted. The design of this array utilizes additional resonators alongside the main resonators to enable harmonic suppression (e.g., the elimination of spurious resonance peaks). As shown, there are resonators having a 3.5 µm diameter, a 8 µm diameter, and a 16 µm diameter. In some embodiments, the diameter of the resonators within the array are between 2 µm-20 µm and comprise any of two, three, or four different diameters arranged in a pattern about a central resonator and configured to suppress one or more resonance peaks.

Figure 20:
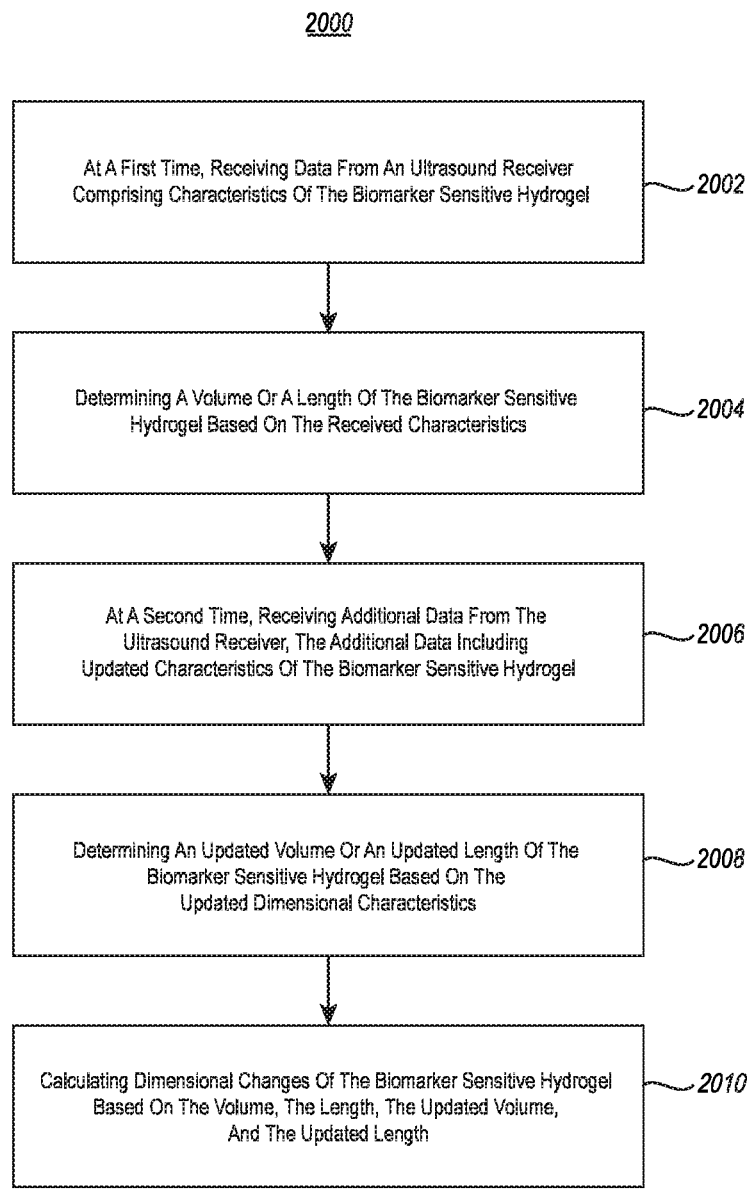
FIG. 20 illustrates an exemplary method for using ultrasound to identify one or more changes in a biomarker sensitive hydrogel positioned within an in vivo environment.

Referring now to FIG. 20, the total kinetic energy of (i) a periodic array of resonators (like that shown in FIG. 17A; solid line) and (ii) an array that enables harmonic suppression (like that shown in FIG. 17B; broken line) are illustrated. As can be seen in the Figure, the total kinetic energy of the periodic array of resonators includes a main mode around 4 MHz with multiple smaller harmonic peaks occurring around 7 MHz, 9 MHz, 13 MHz, and 16 MHz. By including resonators with different sizes and by placing them between the main resonators within the array (as shown in FIG. 17B), the main mode was maintained around 4 MHz, but the next closest harmonic peak—expected to occur around 7 MHz—was suppressed. In some embodiments, the sizes of the side resonators are tuned to suppress specific unwanted peaks.

Implementations of harmonic suppression hydrogel resonator arrays described above can advantageously eliminate or reduce the number and/or frequency of redundant resonance peaks, and in some embodiments, this can consequently make the resonance spectrum easier to track and can additionally clear frequency bands for conventional ultrasound imaging. Additionally, the reduction in the number of spurious peaks can beneficially mitigate the risk of misinterpreting the main resonance peak.

Optical Biomarker Sensitive Hydrogels

Referring now to FIG. 19, illustrated is an embodiment of an optic fiber filament 1902 associated with a biomarker sensitive hydrogel 1904 that dynamically responds to an analyte concentration (e.g., a biomarker concentration) to undergo a volumetric change or a colorimetric change 1906. A volumetric change in the terminally tipped biomarker sensitive hydrogel 1904 can act similar to an optical lens, distorting light entering the optic fiber filament 1902. The distorted light can be used as a readout for determining the volumetric change (and thereby the amount or concentration of biomarker interacting with the biomarker sensitive hydrogel 1904).

In some embodiments, the biomarker sensitive hydrogel 1904 undergoes a colorimetric change 1906. The colorimetric change 1906 causes a shift in the frequency of light entering the optic fiber filament 1902, and in embodiments where the colorimetric change (e.g., darker hue or color shift) is biomarker concentration dependent, the shift in light frequencies entering the optic fiber filament 1902 correlates with the concentration of biomarker interacting with the biomarker sensitive hydrogel 1904.

Methods of Using Ultrasound to Identify Changes in Biomarker Sensitive Hydrogels The following discussion now refers to methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Referring now to FIG. 20, a method 2000 is illustrated. The method 2000 includes acts for using ultrasound to identify one or more changes in a biomarker sensitive hydrogel positioned within an in vivo environment. The method 2000 includes receiving data from an ultrasound receiver, the data comprising one or more characteristics of the biomarker sensitive hydrogel (act 2002). For example, FIG. 8 illustrates a computer system 802 receiving data from an ultrasound receiver 804 comprising characteristics of a biomarker sensitive hydrogel 806.

The method 2000 further includes determining one or more of a volume or a length of the biomarker sensitive hydrogel based on the one or more characteristics (act 2004). For example, FIG. 8 illustrates representations of a computer system 802 determining the volume or length of the biomarker sensitive hydrogel 806, 808 based on characteristics.

The method 2000 further includes at a second time, receiving additional data from the ultrasound receiver, the additional data comprising one or more updated characteristics of the biomarker sensitive hydrogel (act 2006). For example, in FIG. 8, the computer system 802 receives additional data from the ultrasound receiver 804 at a second time that comprises updated characteristics.

The method 2000 may further include determining one or more of an updated volume or an updated length of the biomarker sensitive hydrogel based on the one or more updated characteristics. For example, in FIG. 8, the computer system 802 determines an updated volume or an updated length of the biomarker sensitive hydrogel based on the one or more updated characteristics.

The method 2000 may further include calculating the one or more dimensional changes of the biomarker sensitive hydrogel based on the volume, the length, the updated volume, and the updated length. For example, in FIG. 8, the computer system 802 calculates dimensional changes of the biomarker sensitive hydrogel based on the volume, length, updated volume, and updated length.

Embodiments of the present invention may comprise or utilize a special purpose or general-purpose computer including computer hardware, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Conclusion

Any headings used herein are for organizational purposes only and are not meant to be used to limit the scope of the description or the claims.

Various aspects of the present disclosure, including devices, systems, and methods may be illustrated with reference to one or more embodiments or implementations, which are exemplary in nature. As used herein, the term "exemplary" means "serving as an example, instance, or illustration," and should not necessarily be construed as preferred or advantageous over other embodiments disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," "involves," "contains," etc.), and similar terms as used herein, including within the claims, shall be inclusive and/or open-ended, shall have the same meaning as the word "comprising" and variants thereof (e.g., "comprise" and "comprises"), and do not exclude additional un-recited elements or method steps, illustratively. Unless defined otherwise, all technical and scientific terms used herein have the same meaning as commonly understood by one of ordinary skill in the art to which the present disclosure pertains.

Disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure. Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

Accordingly, the present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. A system for identifying one or more changes in a biomarker sensitive hydrogel configured to be positioned within an in vivo environment, the system comprising:
   a biomarker sensitive hydrogel, the biomarker sensitive hydrogel being configured to be positioned within the in vivo environment and configured to dimensionally change in response to interaction with one or more predefined biomarkers, wherein the biomarker sensitive hydrogel is unconstrained so as to be configured to resonate;
   an ultrasound transducer configured to locate the biomarker sensitive hydrogel within the in vivo environment and configured to identify a shift in acoustic resonance frequency of the biomarker sensitive hydrogel;
   a computer system in electrical communication with the ultrasound transducer, the computer system having one or more processors and being configured to:
      receive, from the ultrasound transducer, data relative to the acoustic resonance frequency of the biomarker sensitive hydrogel; and
      determine, at the one or more processors, one or more changes of the biomarker sensitive hydrogel based on the received data.

2. The system as in claim 1, wherein the computer system receives, from the ultrasound transducer, the one or more characteristics of the biomarker sensitive hydrogel at a first time and at a second time, and wherein the computer system determines, at the one or more processors, the one or more changes of the biomarker sensitive hydrogel based on differences between the one or more characteristics of the biomarker sensitive hydrogel at the first time and at the second time.

3. The system as in claim 2, wherein the biomarker sensitive hydrogel comprises one or more markers or contrast agents, and wherein the differences between the one or more characteristics of the biomarker sensitive hydrogel at the first time and at the second time further comprise (i) a change in an average density of the one or more markers or contrast agents or (ii) a change in a distance between at least two markers or contrast agents of the one or more markers or contrast agents.

4. The system as in claim 1, wherein the system further comprises a control hydrogel configured to be positioned within the in vivo environment, the control hydrogel configured not to dimensionally change in response to interaction with one or more predefined biomarkers,
   wherein the ultrasound transducer is configured to locate the control hydrogel and identify one or more control characteristics of the control hydrogel, and
   wherein the computer system is further configured to receive, from the ultrasound transducer, the one or more control characteristics and determine, at the one or more processors, the one or more changes based on differences between the one or more characteristics of the biomarker sensitive hydrogel and the one or more control characteristics of the control hydrogel.

5. The system as in claim 4, wherein the biomarker sensitive hydrogel and the control hydrogel each comprise one or more markers or contrast agents, the one or more markers or contrast agents comprising one or more of: a metal, a plurality of microspheres, a plurality of microbubbles, a plurality of microwires, a plurality of nanowires, or a plurality of sonically reflective nanoparticles.

6. The system as in claim 5, wherein the one or more markers or contrast agents are positioned to render a plurality of barber pole stripes along or within the biomarker sensitive hydrogel and the control hydrogel or are positioned to render one or more foci along or within the biomarker sensitive hydrogel and the control hydrogel.

7. The system as in claim 1, wherein the biomarker sensitive hydrogel comprises an elongate shape between 10-100 μm thick and 2-20 mm long.

8. The system as in claim 7, wherein the one or more changes comprise a change in a volume of the biomarker sensitive hydrogel, and wherein the change in the volume causes a detectable change in the acoustic resonance frequency of the biomarker sensitive hydrogel and such change in acoustic resonance frequency correlates with a concentration of the one or more predefined biomarkers interacting with the biomarker sensitive hydrogel.

9. The system as in claim 1, wherein the one or more characteristics of the biomarker sensitive hydrogel comprise:
   a first set of characteristics of the biomarker sensitive hydrogel; and
   a second set of characteristics of the biomarker sensitive hydrogel,
   wherein the first set of characteristics of the biomarker sensitive hydrogel correspond to a first view of the biomarker sensitive hydrogel within the in vivo environment,
   wherein the second set of characteristics of the biomarker sensitive hydrogel correspond to a second view of the biomarker sensitive hydrogel within the in vivo environment, and wherein the second view is substantially orthogonal to the first view.

10. The system as in claim 1, wherein the biomarker sensitive hydrogel comprises:
a hydrogel resonator sheet configured to absorb a subset of ultrasonic frequency bands emitted by the ultrasound transducer, the hydrogel resonator sheet comprising a biomarker sensitive hydrogel arranged in an array of acoustic resonators that undergo one or more physical changes in response to a selective association with the one or more biomarkers.

11. The system as in claim 10, wherein the computer system is additionally configured to:
receive, from the ultrasound transducer, a plurality of ultrasound frequencies outside the subset of ultrasonic frequency bands.

12. The system as in claim 10, wherein the one or more characteristics comprise a shift in a frequency position of a maxima of the absorption for the portion of the array of acoustic resonators, and wherein the one or more changes of the hydrogel resonator sheet comprise a swelling or a shrinking of at least the portion of the array of resonators as determined by the shift in the frequency position of the maxima of the absorption for the portion of the array of resonators.

13. The system as in claim 10, wherein the hydrogel resonator sheet is spatially associated with a contrast structure, and wherein the computer system is additionally configured to receive, from the ultrasound transducer, spatial information associated with the contrast structure.

14. The system as in claim 13, wherein the computer system determines the one or more changes based on the spatial information associated with the contrast structure and the received one or more characteristics between a first point in time and a second point in time.

15. The system as in claim 10, wherein the array of acoustic resonators comprises a periodic array of same-sized acoustic resonators.

16. The system as in claim 10, wherein the array of acoustic resonators comprises a repeated pattern of cylindrical ultrasonic resonators to enable selective harmonic suppression, the repeated pattern comprising:
in a first direction, a central cylindrical ultrasonic resonator having a first size alternating with a second cylindrical ultrasonic resonator having a second size; and
in a second direction, the central cylindrical ultrasonic resonator alternating with a third cylindrical ultrasonic resonator having a third size.

17. The system as in claim 16, wherein the central cylindrical ultrasonic resonator comprises a diameter of at least 3.5 μm, wherein the second cylindrical ultrasonic resonator comprises a diameter of at least 8 μm, and wherein the third ultrasonic resonator comprises a diameter of at least 16 μm.

18. The system as in claim 1, wherein the biomarker sensitive hydrogel is unconstrained to allow swelling or shrinking of the hydrogel in multiple dimensions.

19. The system as in claim 1, wherein the system is configured to identify a shift in a frequency position of a maxima of absorption for the biomarker sensitive hydrogel.

20. The system as in claim 1, wherein the ultrasound transducer is particularly configured to emit an ultrasonic frequency that causes the biomarker sensitive hydrogel to resonate.

21. The system as in claim 1, wherein the biomarker sensitive hydrogel is attached to a contrast structure.

22. A computer-implemented method for using ultrasound to identify one or more changes in a biomarker sensitive hydrogel configured to be positioned within an in vivo environment, the method comprising:
at a first time, receiving data from an ultrasound receiver, the data comprising one or more characteristics of the biomarker sensitive hydrogel, wherein the biomarker sensitive hydrogel is unconstrained, so as to be configured to resonate;
determining a resonance frequency or acoustic absorption of the biomarker sensitive hydrogel;
at a second time, receiving additional data from the ultrasound receiver, the additional data comprising one or more updated characteristics of the biomarker sensitive hydrogel;
determining an updated resonance frequency or updated acoustic absorption of the biomarker sensitive hydrogel; and
calculating a concentration of a biomarker based on the resonance frequency or acoustic absorption, and the updated resonance frequency or updated acoustic absorption of the biomarker sensitive hydrogel.

* * * * *